US009561994B2

(12) United States Patent
Shaver et al.

(10) Patent No.: US 9,561,994 B2
(45) Date of Patent: Feb. 7, 2017

(54) PROCESSES FOR PRODUCING ACETIC ACID

(71) Applicant: Celanese International Corporation, Dallas, TX (US)

(72) Inventors: Ronald David Shaver, Houston, TX (US); Yaw-Haw Liu, Missouri City, TX (US); Mark O Scates, Houston, TX (US); Sarah Lane Abrego, Houston, TX (US)

(73) Assignee: CELANESE INTERNATIONAL CORPORATION, Dallas, TX (US)

(*) Notice: Subject to any disclaimer, the term of this patent is extended or adjusted under 35 U.S.C. 154(b) by 0 days.

(21) Appl. No.: 14/874,355

(22) Filed: Oct. 2, 2015

(65) Prior Publication Data
US 2016/0221910 A1 Aug. 4, 2016

Related U.S. Application Data

(63) Continuation-in-part of application No. 14/694,913, filed on Apr. 23, 2015.

(60) Provisional application No. 62/141,490, filed on Apr. 1, 2015, provisional application No. 62/109,765, filed on Jan. 30, 2015.

(51) Int. Cl.
*C07C 51/47* (2006.01)
*C07C 51/12* (2006.01)
*C07C 51/44* (2006.01)

(52) U.S. Cl.
CPC .............. *C07C 51/12* (2013.01); *C07C 51/44* (2013.01); *C07C 51/47* (2013.01)

(58) Field of Classification Search
CPC .................................. C07C 51/47; C07C 51/72
USPC ........................................................ 562/519
See application file for complete search history.

(56) References Cited

U.S. PATENT DOCUMENTS

| 3,769,329 A | 10/1973 | Paulik et al. |
| 3,772,156 A | 11/1973 | Johnson et al. |
| 3,791,935 A | 2/1974 | Eubanks et al. |
| 4,039,395 A | 8/1977 | Eby |
| 4,139,688 A | 2/1979 | Dixon |
| 4,255,591 A | 3/1981 | Makin et al. |
| 4,615,806 A | 10/1986 | Hilton |
| 4,786,699 A | 11/1988 | Nuber et al. |
| 4,994,608 A | 2/1991 | Torrence et al. |
| 5,001,259 A | 3/1991 | Smith et al. |
| 5,026,908 A | 6/1991 | Smith et al. |
| 5,139,981 A | 8/1992 | Kurland |
| 5,144,068 A | 9/1992 | Smith et al. |
| 5,220,058 A | 6/1993 | Fish et al. |
| 5,227,520 A | 7/1993 | Cooper |
| 5,227,524 A | 7/1993 | Jones |
| 5,237,097 A | 8/1993 | Smith et al. |
| 5,286,826 A | 2/1994 | Shih et al. |
| 5,334,755 A | 8/1994 | Yoneda et al. |
| 5,344,976 A * | 9/1994 | Jones ............... C07C 51/573 562/608 |
| 5,391,821 A | 2/1995 | Koyama et al. |
| 5,416,237 A | 5/1995 | Aubigne et al. |
| 5,466,874 A | 11/1995 | Scates et al. |
| 5,625,095 A | 4/1997 | Miura et al. |
| 5,653,853 A | 8/1997 | Kagotani et al. |
| 5,672,744 A | 9/1997 | Kagotani et al. |
| 5,683,492 A | 11/1997 | Hesse et al. |
| 5,696,284 A | 12/1997 | Baker et al. |
| 5,723,660 A | 3/1998 | Morimoto et al. |
| 5,731,252 A | 3/1998 | Warner et al. |
| 5,801,279 A | 9/1998 | Miura et al. |
| 5,831,120 A | 11/1998 | Watson et al. |
| 5,877,347 A | 3/1999 | Ditzel et al. |
| 5,877,348 A | 3/1999 | Ditzel et al. |
| 5,883,295 A | 3/1999 | Sunleu et al. |
| 5,916,422 A | 6/1999 | Kimura et al. |
| 5,932,764 A | 8/1999 | Morris et al. |
| 5,942,460 A | 8/1999 | Garland et al. |
| 5,962,735 A | 10/1999 | Kulprathipanja et al. |
| 6,066,762 A | 5/2000 | Yoneda et al. |

(Continued)

FOREIGN PATENT DOCUMENTS

| CN | 1349855 A | 5/2002 |
| CN | 1640843 A | 7/2005 |
| CN | 101053841 A | 10/2007 |
| EP | 0161874 A1 | 11/1985 |
| EP | 0685445 A1 | 12/1995 |
| EP | 1737808 B1 | 11/2006 |
| JP | 2000-72712 A | 3/2000 |
| WO | 9822420 A1 | 5/1998 |
| WO | 0216297 A1 | 2/2002 |
| WO | 2005085166 A1 | 11/2006 |

OTHER PUBLICATIONS

"The Cativa .TM.Process for the Production of Acetic Acid", Chem. Ind. (Dekker) 1998, 75 Catalysis of Organic Reactions of Derrick J. Watson, pp. 369-380.
Akinori, S. "Acetic Acid Synthesis From Methanol" J. Japan Petroleum Institute 20(5); 379-462 (1977).
English translation of JP2000-72712, Mar. 7, 2000.
English translation of Akinori, S. "Acetic Acid Synthesis From Methanol" J. Japan Petroleum Institute 20(5); 379-462 (1977).

*Primary Examiner* — Sikarl Witherspoon
(74) *Attorney, Agent, or Firm* — Mark L. Cooper; Cooper & Assoc.

(57) ABSTRACT

The disclosure is directed to a carbonylation process for producing acetic acid which includes separating a vapor product stream from a carbonylation reactor to produce a crude acid product comprising acetic acid comprising lithium cations and contacting the crude acetic acid product with a cationic exchanger in the acid form within a first treatment device to produce an intermediate acid product; and contacting the intermediate acetic acid product with a metal-exchanged ion exchange resin having acid cation exchange sites within a second treatment device to produce a purified acetic acid. Embodiments directed to operation of a treatment device comprising a plurality of sampling ports are also disclosed.

19 Claims, 5 Drawing Sheets

(56) References Cited

U.S. PATENT DOCUMENTS

| | | |
|---|---|---|
| 6,143,930 A | 11/2000 | Singh et al. |
| 6,225,498 B1 | 5/2001 | Blay et al. |
| 6,255,527 B1 | 7/2001 | Muskett |
| 6,339,171 B1 | 1/2002 | Singh et al. |
| 6,657,078 B2 | 12/2003 | Scates et al. |
| 7,005,541 B2 | 2/2006 | Cheung et al. |
| 7,208,624 B2 | 4/2007 | Scates et al. |
| 7,223,883 B2 | 5/2007 | Picard et al. |
| 7,223,886 B2 | 5/2007 | Scates et al. |
| 7,271,293 B2 | 9/2007 | Trueba et al. |
| 7,476,761 B2 | 1/2009 | Kojima |
| 7,678,940 B2 | 3/2010 | Miura et al. |
| 7,683,212 B2 | 3/2010 | Kojima et al. |
| 7,838,701 B2 | 11/2010 | Trueba et al. |
| 7,855,306 B2 | 12/2010 | Zinobile et al. |
| 7,884,237 B2 | 2/2011 | Shaver |
| 8,076,507 B2 | 12/2011 | Scates et al. |
| 8,173,076 B2 | 5/2012 | Powell et al. |
| 8,530,696 B2 | 9/2013 | Zinobile |
| 8,697,908 B2 | 4/2014 | Torrence et al. |
| 8,889,904 B2 | 11/2014 | Shaver et al. |
| 8,940,932 B2 | 1/2015 | Shimizu |
| 8,957,248 B2 | 2/2015 | Miura et al. |
| 2006/0011462 A1 | 1/2006 | Horiguchi et al. |
| 2006/0247466 A1 | 11/2006 | Zinobile et al. |
| 2009/0036710 A1 | 2/2009 | Miura et al. |
| 2009/0062525 A1 | 3/2009 | Shibata et al. |
| 2009/0259072 A1 | 10/2009 | Umehara et al. |
| 2011/0288333 A1 | 11/2011 | Shaver et al. |
| 2012/0078012 A1 | 3/2012 | Torrence et al. |
| 2012/0090981 A1 | 4/2012 | Torrence et al. |
| 2012/0132515 A1 | 5/2012 | Ohno |
| 2013/0026458 A1 | 1/2013 | Fukui et al. |
| 2013/0116470 A1 | 5/2013 | Miura et al. |
| 2013/0204014 A1 | 8/2013 | Nishihara et al. |
| 2013/0261334 A1 | 10/2013 | Shimizu et al. |
| 2013/0264186 A1 | 10/2013 | Shimizu et al. |
| 2013/0281735 A1 | 10/2013 | Shimizu et al. |
| 2015/0025270 A1 | 1/2015 | Shimizu et al. |

\* cited by examiner

PROCESSES FOR PRODUCING ACETIC ACID

RELATED APPLICATIONS

This application claims priority to U.S. Provisional Application Ser. No. 62/109,765 filed Jan. 30, 2015, and is a continuation-in-part of U.S. application Ser. No. 14/694,913, filed Apr. 23, 2015, which claims priority benefit to U.S. Provisional Application Ser. No. 62/141,490 filed Apr. 1, 2015, the disclosures of which are each fully incorporated herein by reference.

BACKGROUND

Acetic acid production by carbonylation includes continuously reacting methanol and carbon monoxide in the presence of a catalyst in a reactor. The reaction mixture present in the reactor comprises a transition metal, which may be a Group 9 metal, which may be iridium and/or rhodium, and may further include one or more solvents, water, various stabilizers, co-catalysts, promoters, and the like. Reaction mixtures known in the art may comprise acetic acid, methyl acetate, methyl iodide, hydrogen iodide, a hydrogen iodide promoter, and the like.

A complex network of interdependent equilibria involving liquid acetic acid reaction components exists in the reactor, which include those directed to the formation of acetic acid, as well as those directed to the formation of various impurities which are also produced in the reactor. Impurities which may be present in acetic acid include permanganate reducing compounds (PRCs) such as acetaldehyde. Accordingly, acetic acid processes disclosed in the art may further include various purification processes and control schemes wherein impurity formation is minimized and/or impurities produced are removed from the process or converted into product acetic acid.

Various impurities present in the produce acetic acid are difficult to remove. There is a need to control and monitor purification systems in various aspects of an acetic acid production process.

SUMMARY

In embodiments, a process comprises carbonylating at least one member selected from the group consisting of methanol, dimethyl ether, and methyl acetate in the presence of 0.1 to less than 14 wt. % water, a rhodium catalyst, methyl iodide and lithium iodide, to form a reaction medium comprising acetic acid in a reactor; separating the reaction medium into a liquid recycle stream and a vapor product stream; separating the vapor product stream in up to 2 distillation columns in a primary purification train to produce a crude acid product comprising acetic acid comprising lithium cations; contacting the crude acetic acid product with a first purification resin comprising a cationic exchanger in the acid form within a first treatment device to produce an intermediate acid product; and contacting the intermediate acetic acid product with a second purification resin comprising a metal-exchanged ion exchange resin having acid cation exchange sites within a second treatment device to produce a purified acetic acid stream, the first treatment device, the second treatment device, or both individually comprising at least one sample sampling port disposed through a side of the treatment device; obtaining a sample of the first purification resin, the second purification resin, a liquid sample of the acetic acid stream present in the treatment device, or a combination thereof through the corresponding sample port; and determining a concentration of an impurity in at least one sample.

This summary is provided to introduce a selection of concepts that are further described below in the detailed description. This summary is not intended to identify key or essential features of the claimed subject matter, nor is it intended to be used as an aid in limiting the scope of the claimed subject matter.

DETAILED DESCRIPTION

Figure 1:
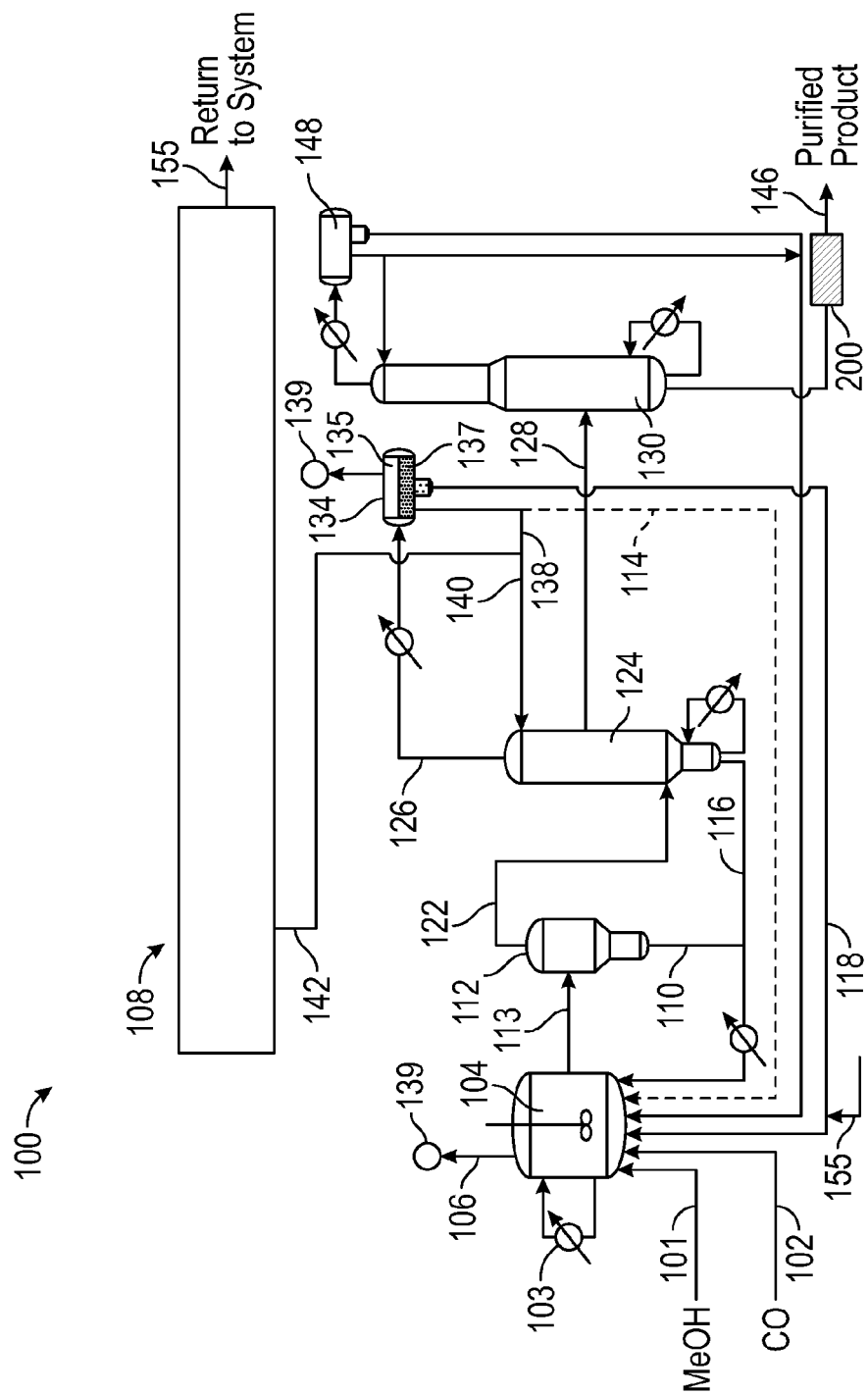
FIG. 1 is a schematic diagram of a process to produce acetic acid according to an embodiment.

At the outset, it should be noted that in the development of any such actual embodiment, numerous implementation—specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the processes disclosed herein can also comprise components other than those cited or specifically referred to, as is apparent to one having minimal skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise indicated.

As used in the specification and claims, "near" is inclusive of "at." The term and/or refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

As used herein, the symbols representative of the elements and the new numbering scheme for the Periodic Table Groups are as used consistent with those disclosed in Chemical and Engineering News, 63(5), 27 (1985). All molecular weights are weight average unless otherwise noted.

All percentages are expressed as weight percent (wt %), based on the total weight of the particular composition or stream present, unless otherwise noted. Room temperature is 25° C. and atmospheric pressure is 101.325 kPa unless otherwise noted.

For purposes herein, the percentage of exchanged active sites of the resin is based on the total exchange capacity in milliequivalents per gram (meq/g). For example, a cationic ion exchange resin having a cation exchange capacity of 2 meq/g, substitution of 2 meq/g with a silver ion constitutes 100% of the active sites being substituted with silver, 1 meq/g substitution constitutes 50% of the active sites being substituted.

For purposes herein:
acetic acid may be abbreviated as "AcOH";
methyl acetate may be abbreviated "MeAc";
methyl iodide may be abbreviated as "MeI"; and
carbon monoxide may be abbreviated "CO".

Permanganate reducing compounds (PRC) refers to oxidizable compounds which cause a fail designation of the permanganate test as is readily understood by one of skill in the art (cf. "A New System For Automatic Measurement of Permanganate Time," Laboratory Automation and Information Management, 34, 1999, 57-67). Examples of permanganate reducing compounds (PRCs) include acetaldehyde, acetone, methyl ethyl ketone, butyraldehyde, crotonaldehyde, 2-ethyl crotonaldehyde, 2-ethyl butyraldehyde, and the like, and the aldol condensation products thereof.

For purposes herein, an "overhead" of a distillation column refers to the lowest boiling condensable fraction which exits at the top, or proximate to the top, of the distillation column. Likewise, the residuum of a distillation column refers to the highest boiling fraction which exits at or near the bottom of the distillation column. It is to be understood that a residuum may be taken from just above the very bottom exit of a distillation column, for example, wherein the very bottom of the column is an unusable tar, a solid waste product, or a de minimis stream as would be readily understood by one of minimal skill in the art. Likewise, the overhead stream may be taken just below the upper most exit of a distillation column, for example, wherein the lowest boiling fraction is a non-condensable stream or represents a de minimis stream, as would be readily understood by one of minimal skill in the art.

As used herein, an average residence time of a column feed stream within a column refers to the total flow rate provided to a column divided by the total unoccupied volume present in the column, unless otherwise stated.

For purposes herein, treatment vessels, which may be referred to as columns, have an inlet and an outlet. The inside of the column, also referred to herein as an inner chamber, is suitable for filling with purification resin. The terms treatment device and column are used interchangeably herein, unless otherwise indicated. For purposes herein, a treatment device and a column other than a distillation column, are used interchangeably.

As used herein, mass flow rate refers to kg/hr unless otherwise stated, and may be determined directly or calculated from volumetric measurements. When a total mass flow rate or a concentration of a component is qualified as being present, "if any", it is to be understood that the component may or may NOT be present in the stream above a detection limit of an appropriate analytical method as readily understood by one of minimal skill in the art.

As used herein, when a mass flow rate of a stream is "controlled" at either a specific flow rate or at a rate which is proportional to a mass flow rate of another stream, it is to be understood that such control includes varying the particular process flow stream directly, or controlling the mass flow of the particular stream by varying streams which directly affect the mass flow rate of the target stream, as readily understood by one of skill in the art. All such ratios are expressed as mass to mass weight percentages unless otherwise stated.

As used herein, a carbonylatable reactant is any material which reacts with carbon monoxide under reaction conditions to produce acetic acid, or the intended product. Carbonylatable reactants include methanol, methyl acetate, dimethyl ether, methyl formate, and the like.

As used herein, a low water carbonylation process is defined as having a finite concentration of water in the carbonylation reactor of less than or equal to about 14 weight percent.

As used herein, when at least a portion of a stream is recycled or directed back into another portion of the process, it is to be understood that a "portion" refers to a portion of the entire mass flow of the stream. The stream may be combined with other streams (i.e., indirectly recycled), yet all of the components originally present in the stream are present after being combined.

In comparison, a stream "derived" from another stream may include the entire stream or may include less than all of the individual components initially present in the stream. A stream "derived" from a particular stream may thus include a stream which is subject to further processing or purification prior to disposition. For example, a stream which is distilled prior to being recycled is derived from the original stream.

As used herein, unless otherwise specified, limitations based on a comparison between an effect observed in the presence of a component relative to the effect observed in the absence of the same component refer to comparisons made under essentially identical conditions except the presence or absence of the identified component (e.g., essentially the same composition, essentially the same temperature, time, and other conditions).

Impurities present in acetic acid include various iodine containing species. Examples include alkyl iodides having from 1 to about 20 carbon atoms. The higher molecular weight alkyl iodides having more than about 6 carbons may be present at parts per billion levels in the final product. These impurities are problematic to various end uses of acetic acid and require removal according to various purity standards. Other impurities include various aldehydes and corrosion metals. These contaminants may be removed by contact of the acetic acid with a suitable purification resin at temperatures greater than about 50° C. (cf. U.S. Pat. No. 6,657,078). The use of such purification resins, however, requires monitoring of both the final product and the resin itself to prevent impurities from "breaking through" the purification resin bed during production.

While samples of the final product are readily obtainable, samples of the purification resin being employed in such purification processes are nearly impossible to obtain while the purification system is in operation. Furthermore, shutdown of such purification systems to obtain resin samples is uneconomical and often dubious. However, a sampling device according to one or more embodiments of the instant disclosure allows for both a liquid sample and a sample of the solid purification resin to be acquired and analyzed at various points along a resin bed. The ability to obtain these samples allows for improved monitoring and control over the process. These sample ports further allow for predicting when a resin will become exhausted prior to excessive amounts of impurities being present in the final product.

In embodiments, a method, comprises providing a column comprising an inner chamber comprising an active purification resin located between a column inlet and a column outlet, the column further comprising one or more sample ports arranged between the column inlet and the column outlet, at least one sample port comprising a liquid sample port, a solid sample port, or both; and flowing an acetic acid stream having a first concentration of an impurity through the column at a temperature and flow rate sufficient to produce a purified acetic acid stream at the column outlet having a second concentration of the impurity, if any, which is less than the first concentration. Accordingly, the acetic acid contacts the purification resin within the column to remove impurities and purify the acetic acid. In embodiments, the method further comprises opening at least one sample port prior to, or simultaneously with flowing the acetic acid stream through the column. In embodiments, the impurity comprises iodine, chromium, nickel, iron, or a combination thereof. In embodiments, the iodide may be an alkyl iodide. In embodiments, the purification resin comprises a macroreticular, strong acid, ion exchange resin having at least about 1 percent active sites in a silver or mercury form, and/or the temperature is at least about 50° C.

In embodiments, the opening of at least one sample port may comprise obtaining a sample of the purification resin through at least one solid sample port, a liquid sample of the acetic acid stream present in the column through at least one liquid sample port, or a combination thereof, and the method further comprises determining a concentration of the impurity in at least one sample.

In embodiments, the concentration of one or more of the impurities is determined using gas chromatography, high pressure liquid chromatograph, atomic absorption, inductively coupled plasma spectroscopy, mass spectroscopy, x-ray fluorescence spectroscopy, or a combination thereof.

In embodiments, the impurity concentration of one or more of the samples is compared to a previously determined impurity concentration value, and a determination is made whether or not the impurity concentration indicates exhaustion of the purification resin at a point in the column corresponding to the location of the sample port from which the sample was obtained. In embodiments, the method may further comprise stopping the flow of acetic acid through the column. In embodiments, the flow of acetic acid is stopped prior to exhaustion of essentially all of the active purification resin present in the column such that the impurity concentration in the product acetic acid does not render the acetic acid unsuitable for a particular end use.

In embodiments, a second column similar to the first column may be provided and the acetic acid flowed through and thus purified in the second column while flow through the first column has been stopped.

In embodiments, while flow is stopped on the column at least a portion of the exhausted resin is regenerating prior to resuming flow of the acetic acid stream through the column to produce the purified acetic acid stream. In embodiments, the regeneration of the exhausted resin comprises removing at least a portion of the exhausted resin from the column and refilling at least a portion of the column with active purification resin. In embodiments, at least a portion of the active resin used to refill the column comprises previously exhausted resin which has been regenerated into active purification resin. In embodiments, at least a portion of the exhausted resin is regenerated into the active purification resin within the column.

In embodiments, a method comprises the steps of: (a) providing a column comprising an inner chamber bound by a plurality of sides radially arranged about a central axis and having an inlet end in fluid communication with, and longitudinally separated from, an outlet end through the inner chamber; (b) directing an amount of purification resin into the inner chamber sufficient to fill a portion of the inner chamber; (c) flowing an aqueous wash fluid from the outlet end through the inner chamber to the inlet end at a flow rate and for a period of time sufficient to wash and/or remove fines from the purification resin; and (d) flowing an acetic acid stream having a first concentration of an impurity through the column at a temperature and flow rate sufficient to produce a purified acetic acid stream at the column outlet having a second concentration of the impurity, if any, which is less than the first concentration.

In embodiments, the column comprises the one or more sample ports arranged between the column inlet and the column outlet, at least one sample port comprising a liquid sample port, a solid sample port, or both, and the method further comprises opening at least one sample port. In embodiments, the aqueous wash fluid is flowed for at least 60 minutes.

In embodiments, after step (c) of flowing an aqueous wash fluid through the column an amount of inert gas is directed into the column inlet to remove a portion of the wash fluid. In embodiments, a back flush flow of acetic acid (from the outlet to the inlet) may then be flowed through the column at a flow rate and for a period of time sufficient to remove essentially all of the vapor from the inner chamber. In embodiments, the removal of the vapor may include opening one or more of the sample ports. In embodiments, the flow rate of the back flush flow of acetic acid is less than or equal to about 0.05 bed volumes per minute, and the period of time is less than or equal to about 30 minutes.

In embodiments, the purification resin is pneumatically directed into the inner chamber of the column by providing fluid communication between the inner chamber and a bottom outlet of a container comprising a slurry comprising the purification resin, followed by applying pressure to a headspace of the container in an amount sufficient to pneumatically transfer at least a portion of the slurry from the container into the inner chamber.

In embodiments, the inner chamber of the column and/or the headspace of the container is purged with an inert gas, e.g., nitrogen, to remove oxygen from the space (i.e., such that the space comprises less than 1 wt % oxygen) prior to charging the column with the purification resin.

In embodiments, a process comprises carbonylating at least one member selected from the group consisting of methanol, dimethyl ether, and methyl acetate in the presence of 0.1 to less than 14 wt. % water, a rhodium catalyst, methyl iodide and lithium iodide, to form a reaction medium comprising acetic acid in a reactor; separating the reaction medium into a liquid recycle stream and a vapor product stream; separating the vapor product stream in up to 2 distillation columns in a primary purification train to produce a crude acid product comprising acetic acid comprising lithium cations; contacting the crude acetic acid product with a first purification resin comprising a cationic exchanger in the acid form within a first treatment device to produce an intermediate acid product; and contacting the intermediate acetic acid product with a second purification resin comprising a metal-exchanged ion exchange resin having acid cation exchange sites within a second treatment device to produce a purified acetic acid stream, the first treatment device, the second treatment device, or both individually comprising at least one sampling port disposed through a side of the treatment device; obtaining a sample of the first purification resin, the second purification resin, a liquid sample of the acetic acid stream present in the treatment device, or a combination thereof through the corresponding sample port; and determining a concentration of an impurity in at least one sample.

In embodiments, the process further comprises comparing the impurity concentration of at least one sample to a previously determined impurity concentration value, and determining if the impurity concentration of the sample indicates exhaustion of the purification resin at a point in the treatment device corresponding to the location of the sample port from which the sample was obtained. In embodiments, the process further comprises stopping the flow of acetic acid through the treatment device prior to exhaustion of essentially all of the active purification resin present in the treatment device, regenerating at least a portion of the exhausted resin and resuming flow of the acetic acid stream through the treatment device to produce the purified acetic acid stream.

In embodiments, the metal-exchanged ion exchange resin comprises at least 1% strong acid exchange sites occupied by silver. In embodiments, the crude acid product comprises up to 10 ppm lithium.

In embodiments, separating the vapor product stream comprises: distilling the vapor product stream in a first distillation column and taking a sidedraw to yield a distilled acetic acid product; and distilling the distilled acetic acid product in a second distillation column to produce a crude acid product comprising acetic acid and lithium cations. In embodiments, the process further comprises a step of adding a potassium salt selected from the group consisting of potassium acetate, potassium carbonate, and potassium hydroxide to the distilled acetic acid product prior to distilling the distilled acetic acid product in a second distillation column; wherein at least a portion of the potassium is removed by the cationic exchanger in the acid form.

In embodiments, the crude acetic acid product is contacted with the cationic exchanger at a temperature from 50° C. to 120° C. In embodiments, the intermediate acetic acid product is contacted with the metal-exchanged ion exchange resin at a temperature from 50° C. to 85° C.; or a combination thereof. In embodiments, the intermediate acetic acid product has a lithium ion concentration of less than 50 ppb.

In embodiments, the cationic exchanger in the acid form comprises a resin of acid-form strong acid cation exchange macroreticular, macroporous or mesoporous resins. In embodiments, the process further comprises treating the purified acetic acid product with a cationic exchange resin to recover any silver, mercury, palladium or rhodium. In embodiments, the water concentration in the reaction medium is controlled from 0.1 to 5 wt %, based on the total amount of reaction medium present.

In embodiments, the process further comprises introducing a lithium compound selected from the group consisting of lithium acetate, lithium carboxylates, lithium carbonates, lithium hydroxide, and mixtures thereof into the reactor to maintain the concentration of lithium acetate from 0.3 to 0.7 wt % in the reaction medium. In embodiments, the process further comprises maintaining the hydrogen iodide concentration from 0.1 to 1.3 wt % in the reaction medium; maintaining the rhodium catalyst concentration from 300 and 3000 wppm in the reaction medium; maintaining the water concentration from 0.1 to 4.1 wt % in the reaction medium; maintaining the methyl acetate concentration from 0.6 to 4.1 wt % in the reaction medium; or a combination thereof.

In embodiments, the process further comprises controlling a butyl acetate concentration in the acetic acid product at 10 wppm or less without directly removing butyl acetate from the acetic acid product. In embodiments, the butyl acetate concentration is controlled by maintaining an acetaldehyde concentration at 1500 ppm or less in the reaction medium; controlling a temperature in the reactor from 150 to 250° C.; controlling a hydrogen partial pressure in the reactor from 0.3 to 2 atm; controlling a rhodium catalyst concentration from 100 to 3000 wppm in the reaction medium; or a combination thereof.

In embodiments, the process further comprises controlling an ethyl iodide concentration in the reaction medium at less than or equal to 750 wppm. In embodiments, the propionic acid concentration in the product acetic acid is less than 250 wppm, without directly removing propionic acid from the product acetic acid, wherein ethyl iodide in the reaction medium and propionic acid in the acetic acid product are present in a weight ratio from 3:1 to 1:2; wherein acetaldehyde and ethyl iodide are present in the reaction medium in a weight ratio from 2:1 to 20:1; wherein an ethanol concentration in the methanol feed into the reactor is less than 150 wppm; or a combination thereof. In embodiments, the ethyl iodide concentration in the reaction medium is controlled by adjusting at least one of a hydrogen partial pressure in the carbonylation reactor, a methyl acetate concentration in the reaction medium, and a methyl iodide concentration in the reaction medium.

Acetic Acid Production System

Processes to produce acetic acid via methanol carbonylation can be conveniently divided into three main areas: the reaction systems and processes, the light ends recovery/acetic acid product separation systems and processes, and the product acetic acid purification systems and processes.

Acetic acid processes suitable for purposes herein to produce the vapor from the carbonylation reactor which is subsequently distilled in the light ends column to yield an acetic acid product as a sidedraw may vary in the systems and processes, including purification streams, recycle streams, the type and number of distillation columns utilized, the various purification processes employed, and the like. Examples of suitable processes include those described in U.S. Pat. Nos. 3,769,329; 3,772,156; 4,039,395; 4,255,591; 4,615,806; 5,001,259; 5,026,908; 5,144,068; 5,237,097; 5,334,755; 5,653,853; 5,683,492; 5,831,120, 5,227,520; 5,416,237, 5,731,252; 5,916,422; 6,143,930; 6,225,498, 6,255,527; 6,339,171; 6,657,078; 7,208,624; 7,223,883; 7,223,886; 7,271,293; 7,476,761; 7,838,71; 7,855,306; 8,076,507; US20060247466; US20090259072; US20110288333; US20120090981; US20120078012; US2012081418; US2013261334; US2013281735; EP0161874; WO9822420; WO0216297; WO2013137236, and the like, the entire contents and disclosure of which are hereby incorporated by reference. A process to produce acetic acid according to embodiments disclosed herein, generally indicated as process 100, is shown schematically in FIG. 1.

Low water and low energy processes for producing acetic acid by the carbonylation of methanol have been developed which involve a rhodium-catalyzed system operating at less than 14 wt. % water and utilizing up to 2 distillation columns in the primary purification train. The primary purification train is directed at removing bulk components, such as water, methyl acetate, methyl iodide, and hydrogen iodide, from the vapor product stream from the reactor/flasher to obtain acetic acid. This primary purification train receives the majority of the vapor flow from the reactor and obtains acetic acid as a final product. For example, the columns of the primary purification train include the light ends column and drying column. This primary purification train may exclude columns whose main function is to remove minor components such as acetaldehyde, alkanes, and propionic acid.

The process for producing acetic acid may generate a cation that is collected in the crude acid product. These residual cations may be difficult to remove and in the final metal-exchange guard bed may adversely replace iodides. Thus, the final product may have unacceptable levels of iodides despite using a metal exchange guard bed. The present invention provides process for removing the cations.

The source of the cation may come from a variety promoters, co-catalysts, additives, in situ reactions, etc. For example low water and low energy processes that involve the use of a promoter such as lithium iodide, which may form in situ following the addition of lithium acetate or other compatible lithium salts to the reaction mixture. Therefore, process streams may contain some quantity of lithium ions. In addition, since the process uses a maximum of 2 distillation columns in the primary purification train and preferable the primary purification does not include a column to remove heavy ends materials, the crude acid product may contain larger alkyl iodide compounds, e.g., $C_{10}$-$C_{14}$ alkyl iodides, in addition to cations, such as lithium. Sometimes more than 10% of the iodides present, or even more than 50%, have an organic chain length of more than 10 carbon atoms. Thus, there may be more than 10 ppb, e.g., more than 20 ppb, more than 50 ppb, more than 100 ppb, or more than 1 ppm of $C_{10}$-$C_{14}$ alkyl iodides. These higher alkyl iodides may be in addition to the usual shorter chain length iodide impurities found in the crude acid product of an iodide promoted carbonylation process, including methyl iodide, HI, and hexyl iodide. The usual iodide impurities are typically removed from the crude acid product using a metal-exchanged strong acid ion exchange resin in which the metal is silver or mercury, for example. However, it has been found that the silver or mercury in the metal-exchanged strong acid ion exchange resin may be displaced by the residual lithium, resulting in lower resin capacity and efficiency and the potential for contaminating the product with silver or mercury.

The cation in the crude acid product may result from the use of organic alkali salt ligands, such as organic lithium salt ligands, such as those described CN101053841 and CN1349855, the entire contents and disclosure of which are hereby incorporated by reference. CN101053841 describes a ligand comprising lithium acetate or lithium oxalate. CN1349855 describes a bimetallic catalyst having a metal lithium organic ligand coordinating cis-dicarbonyl rhodium structure. The metal lithium organic ligand may be a pyridine derivative, such as lithium pyridine-2-formate, lithium pyridine-3-formate, lithium pyridine-4-formate, lithium pyridine-3-acetate, lithium pyridine-4-acetate, or lithium pyridine-3-propionate. In fact, the lithium salt component of all of these ligands are believed to generate lithium iodide in situ within the reaction medium after exposure to methyl iodide at reaction temperature and pressure in the carbonylation reactor. At least some small portion of the lithium component will entrain into the purification system. Thus, purification systems according to the instant disclosure may also remove lithium formed in situ from use of these types of organic ligands.

Cations may also be present as a result of the use of non-lithium salts, such as through the use of bimetallic Rh chelating catalysts that have an amine functionality, such as those described in CN1640543, the entire contents and disclosure of which is hereby incorporated by reference. According to CN16040543 the cation species contains N and O donor atoms and is formed from aminobenzoic acid. The amine may quaternize with methyl iodide in situ within the reaction medium at reaction temperature and pressure to form a quaternary nitrogen cation. The quaternary nitrogen cation, similar to the lithium cation, may be carried through with the crude acid product and may be removed using the present invention prior to the metal-exchange guard beds.

Embodiments include low water and low energy process for producing acetic acid by the carbonylation of methanol, dimethyl ether, and/or methyl acetate in the presence of 0.1 to less than 14 wt. % water, a metal catalyst, methyl iodide and lithium iodide. In embodiments, a low-energy process which utilizes up to 2 distillation columns in the primary purification train (e.g., a light ends column and a water removal or dehydration column without employing a third "heavy ends column) and purifies the resulting acidic acid product with a cationic exchanger in the acid form to remove residual lithium ions followed by treatment with a metal-exchanged ion exchange resin having acid cation exchange sites comprising at least one metal selected from the group consisting of silver, mercury, palladium and rhodium. The metal-exchanged ion exchange resin can have at least 1% of the strong acid exchange sites occupied by silver, mercury, palladium, and/or rhodium, e.g., at least 1% silver, mercury, palladium, and/or rhodium, at least 5% silver, mercury, palladium, and/or rhodium, at least 10% silver, mercury, palladium, and/or rhodium, or at least 20% silver, mercury, palladium, and/or rhodium. By using a cation exchanger to remove lithium prior to the use of a resin having metal-exchanged strong acid cation sites, the displacement of silver, mercury, palladium and/or rhodium from the metal-exchanged sites by the lithium is reduced or eliminated for a process that utilizes up to 2 distillation columns in the primary purification train. In embodiments, other purification systems in addition to the primary purification train may utilize distillation columns to remove impurities from reactor components, such as an aldehyde removal system in which acetaldehyde and other PRCs are removed from the methyl iodide phase before returning the methyl iodide to the reaction medium.

Particularly preferred processes are those utilizing a cation exchanger for removing lithium followed by a silver-exchanged cationic substrate for removing iodides. The crude acid product in many cases includes organic iodides with a $C_{10}$ or more aliphatic chain length which need to be removed. Sometimes more than 10% of the iodides present, e.g., more than 30% or even more than 50%, have an organic chain length of more than 10 carbon atoms.

Decyl iodides and dodecyl iodides are especially prevalent in the absence of heavy ends and other finishing apparatus and are difficult to remove from the product. The silver-exchanged cationic substrates of the present invention typically remove over 90% of such iodides; oftentimes the crude acid product has from 10 to 1000 ppb total iodide prior to treatment which would make the product unusable for iodide-sensitive applications.

An iodide level of 20 ppb to 1.5 ppm in the crude acid product prior to iodide removal treatment is typical; whereas the iodide removal treatment is preferably operative to remove at least about 95% of the total iodide present. In a typical embodiment, lithium/iodide removal treatment involves contacting the crude acid product with a cation exchanger to remove 95% or more of the lithium ions followed by contacting the crude acid product with a silver-exchanged sulfonic acid functionalized macroreticular ion exchange resin, wherein the product has an organic iodide content of greater than 100 ppb prior to treatment and an organic iodide content of less than 10 ppb after contacting the resin.

Lithium has also been found to be entrained in the crude acid product in the absence of heavy ends and other finishing apparatus. Even in very small amounts of 10 ppb of lithium in the crude acid product may cause problem for removing iodides. Up to 10 ppm of lithium by weight of the crude acid product, e.g., up to 5 ppm, up to 1 ppm, up to 500 ppb, up to 300 ppb, or up to 100 ppb, might be present in the acid-containing crude acid product exiting the drying column of an acetic acid process, e.g., the last column in the primary purification train. In terms of ranges, there may be from 0.01 ppm to 10 ppm lithium in the crude acid product, e.g., from 0.05 ppm to 5 ppm or from 0.05 ppm to 1 ppm. By utilizing a cationic exchanger in the acid form before introducing the crude acid product to a metal-exchanged resin, significant amounts of lithium can be removed. For example greater than 90 wt. % of the lithium in the stream might be removed by the cationic exchanger, e.g. 95 wt. % or 99 wt. %. Thus, the stream exiting the acid-form cationic exchanger may contain less than 50 ppb lithium, e.g., less than 10 ppb, or less than 5 ppb. Such removal of the lithium can greatly extend the life of the metal-exchanged resin.

Reaction Systems and Processes

As shown in FIG. 1, the process to produce acetic acid 100 comprises a reaction system which includes the carbonylation reactor 104 from which a portion of the reaction medium is continuously removed via line 113 and subject to flash or low pressure distillation in a separation system, e.g., flasher 112, employed to separate the acetic acid and other volatile components from the reaction medium and recycle the non-volatile components back into the reaction medium via stream 110. The volatile components of the reaction medium are then directed overhead via line 122 into the light ends recovery/acetic acid product separation systems and processes, which begin with light ends column 124.

As shown in FIG. 1, a methanol-containing feed stream 101 and a carbon monoxide-containing feed stream 102 are directed into a liquid phase reaction medium of the carbonylation reactor 104, in which the carbonylation reaction occurs in a reaction medium comprising the catalyst, water, methyl iodide, methyl acetate, acetic acid, an iodide salt, HI, and other reaction medium components.

In embodiments, the carbonylation reactor 104 may be a stirred vessel, a bubble-column type vessel, or a combination thereof, within which the reacting liquid or slurry contents are maintained at levels consistent with normal operation. In embodiments, carbon monoxide may be continuously introduced into the reaction medium of the carbonylation reactor, including below an agitator used to stir the contents. The gaseous feed preferably is thoroughly dispersed through the reacting liquid by this stirring means. In embodiments, the reactor system may further include a number of recycle lines, wherein various components are recycled back into the reaction medium from other parts of the process, and various vapor purge lines, which may be subject to additional processing and the like. It is to be understood that all vents and other vapor purge lines are connected to one or more scrubber systems 139, and that all condensable components are eventually recycled back into the carbonylation reactor prior to the vapor stream being released into the atmosphere, as readily understood by one of minimal skill in the art.

In embodiments, a gaseous purge stream 106 may be vented from reactor 104 to a scrubber system 139 to prevent buildup of gaseous by-products and to control a carbon monoxide partial pressure and/or a total reactor pressure. The reactor system may further include a pump around loop 103 to control the temperature of the reactor In embodiments, the reaction medium comprises a metal catalyst, or a Group 9 metal catalyst, or a catalyst comprising rhodium and/or iridium. In embodiments, the reaction medium comprises a rhodium catalyst.

In embodiments, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. In embodiments, the rhodium component of the catalyst system may be provided by introducing into the reaction zone rhodium in the form of rhodium metal, rhodium salts such as the oxides, acetates, iodides, carbonates, hydroxides, chlorides, and the like, or other compounds that result in the formation of a coordination compound of rhodium in the reaction environment. In alternative embodiments, the carbonylation catalyst comprises rhodium dispersed in a liquid reaction medium or supported on an inert solid. The rhodium can be introduced into the reaction system in any of many forms, and the exact nature of the rhodium moiety within the active catalyst complex may be uncertain.

In embodiments, the catalyst concentration is maintained in the reactor in amounts from about 200 to about 5000 parts per million (ppm) by weight, based on the total weight of the reaction medium.

In embodiments, the reaction medium may further comprise a halogen-containing catalyst promoter. Suitable examples include organic halides, alkyl, aryl, and substituted alkyl or aryl halides. In embodiments, the halogen-containing catalyst promoter is present in the form of an alkyl halide in which the alkyl radical corresponds to the alkyl radical of the feed alcohol which is being carbonylated. Thus, in the carbonylation of methanol to acetic acid, the halide promoter will include methyl halide, or methyl iodide (MeI). In embodiments, the reaction medium comprises greater than or equal to about 5 weight percent MeI, based on the total weight of the reaction medium. In embodiments, the reaction medium comprises greater than or equal to about 5 weight percent and less than or equal to about 50 weight percent MeI. In embodiments, the reaction medium comprises greater than or equal to about 7 weight percent, or 10 weight percent MeI, and less than or equal to about 30 weight percent, or 20 weight percent MeI based on the total weight of the reaction medium.

In embodiments, the liquid reaction medium employed may include any solvent compatible with the catalyst system and may include pure alcohols, or mixtures of the alcohol feedstock and/or the product carboxylic acid and/or esters of these two compounds. In embodiments, the solvent utilized in the liquid reaction medium comprises acetic acid (AcOH). In embodiments, the reaction medium comprises greater than or equal to about 50 weight percent AcOH. In embodiments, the reaction medium comprises greater than or equal to about 50 weight percent and less than or equal to about 90 weight percent AcOH. In embodiments, the reaction medium comprises greater than or equal to about 50 weight percent, or 60 weight percent AcOH, and less than or equal to about 80 weight percent or 70 weight percent AcOH, based on the total weight of the reaction medium.

In embodiments, the reaction medium comprises at least a finite concentration of water. In embodiments, the reaction medium comprises a detectable amount of water. In embodiments, the reaction medium comprises greater than or equal to about 0.001 weight percent water. In embodiments, the reaction medium comprises greater than or equal to about 0.001 weight percent and less than or equal to about 14 weight percent water. In embodiments, the reaction medium comprises greater than or equal to about 0.05 weight percent, or 0.1 weight percent, or 0.5 weight percent, or 1 weight percent, or 2 weight percent, or 3 weight percent, or 4 weight percent water, and less than or equal to about 10 weight percent or 5 weight percent water, based on the total weight of the reaction medium.

In embodiments, the reaction medium further comprises an ester of the carboxylic acid product and the alcohol used in the carbonylation. In embodiments, the reaction medium comprises methyl acetate. In embodiments, the reaction medium comprises greater than or equal to about 0.5 weight percent methyl acetate (MeAc). In embodiments, the reaction medium comprises greater than or equal to about 1 weight percent and less than or equal to about 50 weight percent MeAc. In embodiments, the reaction medium comprises greater than or equal to about 1.5 weight percent, or 2 weight percent, or 3 weight percent MeAc, and less than or equal to about 20 weight percent or 10 weight percent MeAc, based on the total weight of the reaction medium.

In embodiments, the reaction medium further comprises an additional iodide ion that is over and above the iodide ion that is present as hydrogen iodide. In embodiments, the iodide ion concentration is provided by an iodide salt, or lithium iodide (LiI). In embodiments, the reaction medium is maintained under low water concentrations wherein methyl acetate and lithium iodide are present in concentrations sufficient to act as rate promoters (cf. U.S. Pat. No. 5,001,259).

In embodiments, at least a portion of the iodide ion concentration in the reaction medium results from a metal iodide salt, or an iodide salt of an organic cation, or cations based on quaternary amines, phosphines, and the like. In embodiments, the iodide is a metal salt, a Group I or Group 2 iodide salt. In embodiments, the reaction medium comprises an alkali metal iodide, or lithium iodide. In embodiments, the iodide concentration is over and above the iodide ion present as hydrogen iodide. In embodiments, the reaction medium comprises an amount of an iodide salt, or lithium iodide, in an amount sufficient to produce a total iodide ion concentration greater than about 2 weight percent. In embodiments, the reaction medium comprises an amount of an iodide salt, or lithium iodide, in an amount sufficient to produce a total iodide ion concentration greater than or equal to about 2 weight percent and less than or equal to about 40 weight percent, based on the total weight of the reaction medium. In embodiments, the reaction medium comprises greater than or equal to about 5 weight percent, or 10 weight percent, or 15 weight percent iodide ion, and less than or equal to about 30 weight percent or 20 weight percent iodide ion, based on the total weight of the reaction medium.

In embodiments, the reaction medium may further comprise hydrogen, determined according to a hydrogen partial pressure present in the reactor. In embodiments, the partial pressure of hydrogen in the reactor is greater than or equal to about 0.7 kPa (0.1 psia), or 3.5 kPa (0.5 psia), or 6.9 kPa (1 psia), and less than or equal to about 1.03 MPa (150 psia), or 689 kPa (100 psia), or 345 kPa (50 psia), or 138 kPa (20 psia).

In embodiments, the reactor temperature i.e., the temperature of the reaction medium, is greater than or equal to about 150° C. In embodiments, the reactor temperature is greater than or equal to about 150° C. and less than or equal to about 250° C. In embodiments, the reactor temperature is greater than or equal to about 180° and less than or equal to about 220° C.

In embodiments, the carbon monoxide partial pressure in the reactor is greater than or equal to about 200 kPa. In embodiments, the CO partial pressure is greater than or equal to about 200 kPa and less than or equal to about 3 MPa. In embodiments, the CO partial pressure in the reactor is greater than or equal to about the 300 kPa, or 400 kPa, or 500 kPa and less than or equal to about 2 MPa, or 1 MPa. The total reactor pressure represents the combined partial pressure of all reactants, products, and by-products present therein. In embodiments, the total reactor pressure is greater than or equal to about 1 MPa and less than or equal to about 4 MPa.

In embodiments, the liquid reaction medium is drawn off from the carbonylation reactor 104 and directed into the flasher 112 having a lower pressure than is present in the reactor at a rate sufficient to maintain a constant level therein, and is introduced to the flasher 112 at a point intermediate between the top and bottom thereof. In the flasher the less volatile components, namely the catalyst solution, are withdrawn as a base stream 110 (predominantly acetic acid containing the rhodium and the iodide salt along with lesser quantities of methyl acetate, methyl iodide, acetic acid and water) and recycled back into the reaction medium. The overhead of the flasher 122 comprises largely the product acetic acid along with methyl iodide, methyl acetate, water, and PRCs. A portion of the carbon monoxide along with gaseous by-products such as methane, hydrogen, carbon dioxide, and the like may also exit the top of the flasher.

Light Ends Recovery/Acetic Acid Product Separation Systems and Processes

In embodiments, the overhead stream from flasher 112 is directed to the light ends column 124, also referred to in the art as the stripper column, as stream 122, where distillation yields a low-boiling overhead vapor stream 126, also referred to herein as a first overhead stream 126, and a purified acetic acid product stream 128, which in embodiments is removed as a side stream. The light ends column 124 further produces a high boiling residuum stream 116, which may be subject to further purification and/or may be recycled back into the reaction medium.

In embodiments, the first overhead 126 is condensed and then directed into an overhead phase separation unit 134, also referred to herein an overhead decanter. In embodiments, the first overhead 126 comprises methyl iodide, methyl acetate, acetic acid, water, and at least one PRC. In embodiments, the condensed first overhead stream 126 is separated into a light aqueous phase 135 comprising water, acetic acid, methyl iodide, methyl acetate, and at least one permanganate reducing compound (PRC), e.g., acetaldehyde; and a heavy phase 137 comprising methyl iodide, methyl acetate, which may also comprise at least one PRC.

In embodiments, at least a portion of the heavy phase 137, at least a portion of the light phase 135, or a combination thereof is returned to the reaction medium via lines 118 and 114, respectively. In embodiments, a portion of the light phase stream 135 may be recycled to the reaction medium in stream 114, to provide water to the reaction medium as required. In embodiments, the heavy phase 137 is recirculated to the reactor via 118.

In embodiments, the light phase 135, the heavy phase 137, or a combination thereof, is directed to one or more purification processes 108, e.g., an aldehyde removal system, via stream 142. The subsequently purified stream is then returned to the process via one or more streams, collectively referred to as 155.

Although the specific compositions of light liquid phase 135 may vary widely, some exemplary compositions are provided below in Table 1.

TABLE 1

Exemplary Light Liquid Phase from Light Ends Overhead

| Component | conc. (Wt. %) | conc. (Wt. %) | conc. (Wt. %) |
| --- | --- | --- | --- |
| Water | 40-80 | 50-75 | 70-75 |
| Methyl Acetate | 1-50 | 1-25 | 1-15 |
| Acetic Acid | 1-40 | 1-25 | 5-15 |
| PRC's | <5 | <3 | <1 |
| Methyl Iodide | <10 | <5 | <3 |

In an embodiment, overhead decanter 134 is arranged and constructed to maintain a low interface level to prevent an excess hold up of methyl iodide. Although the specific compositions of heavy liquid phase 137 may vary widely, some exemplary compositions are provided below in Table 2.

TABLE 2

Exemplary Heavy Liquid Phase from Light Ends Overhead

| Component | conc. (Wt. %) | conc. (Wt. %) | conc. (Wt. %) |
| --- | --- | --- | --- |
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

Although not shown a portion of light liquid phase 135 and/or heavy liquid phase 137 may be separated and directed to acetaldehyde or PRC removal system to recover methyl iodide and methyl acetate, while removing acetaldehyde. As shown in Tables 1 and 2, light liquid phase 135 and/or heavy liquid phase 137 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 135 and/or heavy liquid phase 137 fed to the acetaldehyde or PRC removal system may vary from 1% to 99% of the mass flow of either the light liquid phase 133 and/or heavy liquid phase 134, e.g., from 1 to 50%, from 2 to 45%, from 5 to 40%, 5 to 30% or 5 to 20%. Also in some embodiments, a portion of both the light liquid phase 135 and heavy liquid phase 137 may be fed to the acetaldehyde or PRC removal system. The portion of the light liquid phase 135 not fed to the acetaldehyde or PRC removal system may be refluxed to the first column or recycled to the reactor, as described herein. The portion of the heavy liquid phase 137 not fed to the acetaldehyde or PRC removal system may be recycled to the reactor. Although a portion of heavy liquid phase 137 may be refluxed to the first column, it is more desirable to return the methyl iodide enriched heavy liquid phase 137 to the reactor.

In one embodiment, a portion of light liquid phase 135 and/or heavy liquid phase 137 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 137 is treated in the PRC removal system, it may be desirable to return a portion the raffinate to either the distillation column or reactor. Also, for example, when light liquid phase 135 is treated in the PRC removal system, it may be desirable to return a portion the raffinate to either the first column, overhead decanter, or reactor. In some embodiments, the extractant may be further distilled to remove water, which is returned to the one or more extraction stages. in which contains more methyl acetate and methyl iodide than light liquid phase 135, may also be recycled to reactor 104 and/or refluxed to first column 124.

Suitable purification processes include those disclosed in U.S. Pat. Nos. 6,143,930, 6,339,171, 7,223,883, 7,223,886, 8,076,507, US20130303800, US20130310603, US20090036710, US20090062525, US20120132515, US20130026458, US201300116470, US20130204014, US20130261334, US20130264186, or US201330281735, all of which are incorporated by reference herein.

Product Purification System and Processes

In embodiments, acetic acid stream 128 may be subjected to further purification, such as in a drying column 130, wherein the acetic acid is collected as a column bottom and the aqueous overhead is collected in an overhead decanter 148, a portion of which may be refluxed back into the drying column 130 prior to being returned to the reactor 104. Other embodiments include directing the acetic acid to a heavy ends column (cf. WO0216297), and/or contacted with one or more absorbent, adsorbent, or ion exchange resins in a resin bed or guard column 200 to remove various impurities (cf. U.S. Pat. No. 6,657,078), and the like in the product purification section of the process, as described more fully herein. As shown, drying column 130, separates acetic acid sidedraw 128 into overhead stream comprised primarily of water and bottoms stream comprised primarily of acetic acid. Overhead stream is cooled and condensed in a phase separation unit, e.g., decanter 148, to form a light phase and a heavy phase. As shown, a portion of the light phase is refluxed and the remainder of the light phase is returned to the reactor. The heavy phase, which typically is an emulsion comprising water and methyl iodide, preferably is returned in its entirety to the reactor. Exemplary compositions for the light phase of the drying column overhead are provided below in Table 3.

TABLE 3

Exemplary Light Phase Compositions from Drying Column Overhead

| | conc. (Wt. %) | conc. (Wt. %) | conc. (Wt. %) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |

In embodiments minor amounts of an alkali component such as KOH can be added to sidedraw 128 prior to entering the drying column 130. In other embodiments, the alkali component might also be added to the drying column 130 at the same height level as the stream 128 entering the drying column 130 or at a height above the height level height level as the stream 128 entering the drying column 130. Such addition can neutralize HI in the column.

In embodiments, the drying column bottoms stream may comprise or consists essentially of acetic acid. In embodiments, drying column bottoms stream comprises acetic acid in an amount greater than 90 wt. %, e.g., greater than 95 wt. % or greater than 98 wt. %. In embodiments, this stream will also be essentially anhydrous, for example, containing less than 0.15 wt. % water, e.g., less than 0.12 wt. % water or less than 0.1 wt. % water. However, as discussed, the stream may contain varying levels of impurities.

In FIG. 1, the crude acid product is withdrawn as a residue in drying column bottoms stream 146. In embodiments, the crude acid product from the drying column 130 may be taken from a side stream at a position slightly above the bottom of the column 130. This side stream may be withdrawn in the liquid or vapor phase. When withdrawn in the vapor phase further condensing and cooling may be necessary prior to removing alkaline contaminants, e.g., lithium contaminants. For example, the crude acid product may be taken as a side stream from a lower part of the column, while a residue stream from the base of the drying column 130 is withdrawn and removed or recycled. This side stream contains the crude acetic acid product that is sent to cationic exchange resin to remove lithium. This can allow for the separation of a higher boiling point fraction from the crude acid product in residue stream. In embodiments, the residue stream is discarded or purged from the process 100.

In embodiments, the crude acid product produced by the drying column 130 is further processed, by passing through a series of metal functionalized iodide removal ion exchange resins, prior to being stored or transported for commercial use. In embodiments, the process for producing acetic acid further includes introducing a lithium compound into the reactor to maintain the concentration of lithium acetate in an amount from 0.3 to 0.7 wt % in the reaction medium. In embodiments, an amount of the lithium compound is introduced into the reactor to maintain the concentration of hydrogen iodide in an amount from 0.1 to 1.3 wt % in the reaction medium. In embodiments, the concentration of the rhodium catalyst is maintained in an amount from 300 to 3000 wppm in the reaction medium, the concentration of water is maintained in amount from 0.1 to 4.1 wt % in the reaction medium, and the concentration of methyl acetate is maintained from 0.6 to 4.1 wt % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \leftrightharpoons \text{LiI} + \text{HOAc} \qquad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %, when determined according to perchloric acid titration to a potentiometric endpoint.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % results in a lack of control over hydrogen iodide concentrations within the reaction medium.

In embodiments, the lithium compound may be introduced continuously or intermittently into the reaction medium. In embodiments, the lithium compound is introduced during reactor start up. In embodiments, the lithium compound is introduced intermittently to replace entrainment losses.

A series of experiments conducted to demonstrate the promotional effect of lithium acetate in the carbonylation reactor and to determine the effect of lithium acetate on the methyl iodide oxidative addition to the rhodium complex, Li[RhI$_2$(CO)$_2$] confirmed the promotional effect of lithium acetate on reaction rates. A linear increase of reaction rates correlated to increasing lithium acetate concentrations was observed. This correlation was indicative of first order promotional effects of reaction between methyl iodide and Li[RhI$_2$(CO)$_2$]. These experiments further showed a non-zero intercept, confirming that lithium acetate is not required for the MeI—Rh(I) reaction to occur, but the lithium acetate does give considerable promotional effect even at low concentrations.

In embodiments, the process may further comprise maintaining a butyl acetate concentration in the acetic acid product at 10 wppm or less without directly removing butyl acetate from the product acetic acid. In embodiments, the butyl acetate concentration in the final acetic acid product may be maintained below 10 ppm by removing acetaldehyde from the reaction medium, e.g., removing acetaldehyde from a stream derived from the reaction medium, and/or by controlling the reaction temperature, and/or the hydrogen partial pressure, and/or the metal catalyst concentration in the reaction medium. In embodiments, the butyl acetate concentration in the final acetic acid product is maintained by controlling one or more of the carbonylation reaction temperature from 150° C. to 250° C., the hydrogen partial pressure in the carbonylation reactor at from 0.3 to 2 atm, the rhodium metal catalyst concentration in the reaction medium at from 100 to 3000 wppm, based on the total weight of the reaction medium, and/or the acetaldehyde concentration in the reaction medium at 1500 ppm or less.

In embodiments, the acetic acid product formed according to embodiments of the process disclosed herein has a butyl acetate concentration of less than or equal to 10 wppm, or less than or equal to 9 wppm, or less than or equal to 8 wppm, or less than or equal to 6 wppm, or less than or equal to 2 wppm, based on the total weight of the acetic acid product. In embodiments, the acetic acid product is substantially free of butyl acetate, i.e., a butyl acetate concentration of less than 0.05 wppm or is non-detectable by detection means known in the art. In embodiments, the acetic acid product may also have a propionic acid concentration of less than 250 wppm, or less than 225 ppm, or less than 200 wppm.

In embodiments, the butyl acetate concentration in the acetic acid product may be controlled by controlling the concentration of acetaldehyde in the reaction medium. While not wishing to be bound by theory, butyl acetate is thought to be a by-product caused by aldol condensation of acetaldehyde. Applicant has discovered that by maintaining the acetaldehyde concentration in the reaction medium at less than 1500 wppm, the concentration of butyl acetate in the final acetic acid product may be controlled below 10 wppm. In embodiments, the acetaldehyde concentration in the reaction medium is maintained at less than or equal to 1500 wppm, or less than or equal to 900 wppm, or less than or equal to 500 wppm, or less than or equal to 400 wppm, based on the total weight of the reaction medium.

In embodiments, the butyl acetate concentration in the acetic acid product may be controlled by controlling the reaction temperature of the carbonylation reactor at a temperature greater than or equal to 150° C., or 180° C., and less than or equal to 250° C., or 225° C.; and/or the hydrogen partial pressure in the carbonylation reactor may be controlled at greater than or equal to 0.3 atm, or 0.35 atm, or 0.4 atm, or 0.5 atm, and less than or equal to 2 atm, or 1.5 atm, or 1 atm.

While relatively high hydrogen partial pressure results in improved reaction rates, selectivity, improved catalyst activity, and reduced temperatures, applicant has discovered that as hydrogen partial pressure is increased, impurity production is also increased, including butyl acetate.

In embodiments, the hydrogen partial pressure may be controlled by modifying the amount of hydrogen present in the carbon monoxide source and/or by increasing or decreasing the reactor vent flows to obtain the desired hydrogen partial pressure within the carbonylation reactor.

A series of experiments were conducted to demonstrate the effect of hydrogen partial pressure and acetaldehyde concentration in the reaction medium on the concentration of butyl acetate in the final acetic acid product. These experiments confirmed a correlation between reduced butyl acetated concentrations in the final acetic acid product, and relatively low acetaldehyde concentrations in the reaction medium and/or relatively low hydrogen partial pressures in the carbonylation reactor. Experiments in which the acetaldehyde concentration in the reactor was maintained below 1500 ppm and the reactor hydrogen partial pressure maintained below 0.6 atm resulted in butyl acetate levels below 10 wppm in the final acetic acid product. Other experiments showed an acetaldehyde concentration in the reactor below 1500 wppm and a reactor hydrogen partial pressure of 0.46 atm resulted in a butyl acetate concentration of less than 8 wppm in the final acetic acid product. Similar conditions in which the hydrogen partial pressure was 0.30 atm resulted in butyl acetate levels below 6 wppm, and hydrogen partial pressures of 0.60 atm resulted in butyl acetate concentrations below 0.2 wppm in the final acetic acid product. However, comparative experiments in which the hydrogen partial pressure was 0.4 and 0.3 respectively, but in the absence of an aldehyde removal system such that the acetaldehyde concentrations in the reactor exceeded 1500 wppm, resulted in a final acetic acid product having butyl acetate levels of 13 wppm and 16 wppm respectively.

Applicant has further discovered that the concentration of propionic acid in the final acetic acid product may be affected by the concentration butyl acetate in the acetic acid product. Accordingly, by controlling the butyl acetate concentration in the final acetic acid product to 10 wppm or less, the concentration of propionic acid in the final acetic acid product may be controlled to less than 250 wppm, or less than 225 ppm, or less than 200 wppm. Likewise, by controlling the ethanol content in the reactor feed, which may be present as an impurity in the methanol source, the propionic acid and butyl acetate concentrations in the final acetic acid product may also be controlled. In embodiments, the concentration of ethanol in the methanol feed to the carbonylation reactor is controlled to less than or equal to 150 wppm. In embodiments, if present, the ethanol concentration in the methanol feed to the reactor is less than or equal to 100 wppm, or 50 wppm, or 25 wppm.

Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the concentration of ethyl iodide in the reaction medium is maintained/controlled to be less than or equal to 750 wppm, or less than or equal to 650 wppm, or less than or equal to 550 wppm, or less than or equal to 450 wppm, or less than or equal to 350 wppm. In alternative embodiments, the concentration of ethyl iodide in the reaction medium is maintained/controlled at greater than or equal to 1 wppm, or 5 wppm, or 10 wppm, or 20 wppm, or 25 wppm, and less than or equal to 650 wppm, or 550 wppm, or 450 wppm, or 350 wppm.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2, or from 5:2 to 1:2, or from 2:1 to 1:2. In embodiments, the acetaldehyde:ethyl iodide concentration in the reaction medium is maintained at a weight ratio from 2:1 to 20:1, or from 15:1 to 2:1, or from 9:1 to 2:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

A series of experiments conducted to determine the effect of acetaldehyde and other reaction conditions on the formation of ethyl indicated a relationship between acetaldehyde concentration and ethyl iodide concentration in the reaction medium, as well as relationships between the reactor concentration of ethyl iodide and the concentration of propionic acid in the final acetic acid product. In general, an ethyl iodide concentration of less than 750 wppm and an acetaldehyde concentration of less than 1500 wppm in the reaction medium resulted in propionic acid concentrations of less than 250 wppm in the acetic acid product.

Iodide Removal Beds/Use of Ion Exchange Resins

In embodiments the product acetic acid streams may be contaminated with halides (e.g., iodides) and lithium may be contacted with an acid-form cationic exchange resin followed by a metal-exchanged ion exchange resin having acid cation exchange sites comprising at least one metal selected from the group consisting of silver, mercury, palladium and rhodium under a range of operating conditions. In embodiments, the ion exchange resin compositions are provided in fixed beds. The use of fixed iodide removal beds to purify contaminated carboxylic acid streams is well documented in the art (see, for example, U.S. Pat. Nos. 4,615,806; 5,653,853; 5,731,252; and 6,225,498, which are hereby incorporated by reference in their entireties). Generally, a contaminated liquid carboxylic acid stream is contacted with the aforementioned ion exchange resin compositions, by flowing through a series of static fixed beds. The lithium contaminants are removed by the cationic exchanger in the acid form. The halide contaminants, e.g., iodide contaminants, are then removed by reaction with the metal of the metal-exchanged ion exchange resin to form metal iodides. In some embodiments, hydrocarbon moieties, e.g., methyl groups that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

Similar iodide contamination issues may exist in acetic anhydride manufactured via a rhodium-iodide catalyst system. Thus, the inventive process may alternatively be utilized in the purification of crude acetic anhydride product streams.

Suitable acid-form cation exchangers for removing metal ion contaminants in the present invention may comprise strong acid cation exchange resins, for example strong acid macroreticular or macroporous resins, for example Amberlyst® 15 resin (DOW), Purolite C145, or Purolite CT145. The resin may also be an acid-form strong acid cation exchange mesoporous resin. Chelating resins and zeolites may also be used.

Suitably stable ion exchange resins utilized in connection with the present invention for preparing silver or mercury-exchanged resins for iodide removal typically are of the "RSO3H" type classified as "strong acid," that is, sulfonic acid, cation exchange resins of the macroreticular (macroporous) type. Particularly suitable ion exchange substrates include Amberlyst® 15, Amberlyst® 35 and Amberlyst® 36 resins (DOW) suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic exchange substrates are disclosed, for example, in U.S. Pat. No. 5,962,735, the disclosure of which is incorporated herein by reference.

At temperatures greater than about 50° C., the silver or mercury exchanged cationic substrate may tend to release small amounts of silver or mercury on the order of 500 ppb or less and thus the silver or mercury exchanged substrate is chemically stable under the conditions of interest. More preferably, silver losses are less than 100 ppb into the organic medium and still more preferably less than 20 ppb into the organic medium. Silver losses may be slightly higher upon start up. In any event, if so desired a bed of acid form cationic material maybe placed downstream of the silver or mercury exchange material in addition to the bed of acid form cationic material upstream of the silver or mercury exchange material, to catch any silver or mercury released.

The pressures during the contacting steps with the exchange resins are limited only by the physical strength of the resins. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) and 118° C. (the boiling point of acetic acid). It is within the purview of those skilled in the art to determine analogous ranges for product streams comprising other carboxylic acid compounds. The temperature of the contacting step preferably is kept low enough to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin significant degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for lithium and/or halide removal.

The configuration of the resin beds within an acetic acid purification train may vary, but the cationic exchanger should be upstream of the metal-exchanged resin. In a preferred embodiment, the resin beds are configured after a final drying column. Preferably the resin beds are configured in a position wherein the temperature of the crude acid product is low, e.g., less than 120° C. or less than 100° C. The stream contacting the acid-form cationic exchange resin and the stream contacting the metal-exchanged resin can be adjusted to the same or different temperatures. For example, the stream contacting the acid-form cationic exchange resin can be adjusted to a temperature of from 25° C. to 120° C., e.g., 25° C. to 85° C., 40° C. to 70° C., e.g., 40° C. to 60° C., while the stream contacting the metal-exchanged resin can be adjusted to a temperature of from 50° C. to 100° C., e.g., 50° C. to 85° C., 55° C. to 75° C., or 60° C. to 70° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

Referring back to FIG. 1, drying column bottoms stream is first passed through cationic exchange resin bed 200 to remove lithium ions. Although one cationic exchange resin bed 200 is shown, it should be understood that a plurality of cationic exchange resin beds may be used in series or parallel. The cationic exchange bed may also remove other cations present in the stream, such as potassium, if added to drying column 130 as a potassium salt selected from the group consisting of potassium acetate, potassium carbonate, and potassium hydroxide, and corrosion metals. The resulting exchanged stream, e.g., an intermediate acid product may then be passed through a metal-exchanged ion exchange resin bed having acid cation exchange sites comprising at least one metal selected from the group consisting of silver, mercury, palladium and rhodium to remove iodides from the stream to produce a purified product 146. Although the purification resins are shown via block 200, it should be understood that a plurality of metal-exchanged ion exchange resin beds may be used in series or parallel. In addition to the resin beds, heat exchangers (not shown) may be located before either resin bed to adjust the temperature of the stream 146 and 182 to the appropriate temperature before contacting the resin beds. Similarly a crude acetic acid product may be fed to a cationic exchange resin bed from a drying column side stream. Heat exchangers or condensers may be located before either resin bed to adjust the temperature of the stream to the appropriate temperature before contacting the resin beds.

In one embodiment, the flow rate through the resin beds ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

A purified acetic acid composition is obtained as a result of the resin bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb lithium, e.g., less than 50 wppb, less than 20 wppb, or less than 10 wppb. In terms of ranges, the purified acetic acid composition may comprise from 0 to 100 wppb iodides, e.g., from 0 to 50 wppb; and/or from 0 to 100 wppb lithium, e.g., from 1 to 50 wppb. In other embodiments, the resin beds remove at least 25 wt % of the iodides from the crude acetic acid product, e.g., at least 50 wt % or at least 75 wt %. In one embodiment, the resin beds remove at least 25 wt % of the lithium from the crude acetic acid product, e.g., at least 50 wt % or at least 75 wt %.

Accordingly, in embodiments, the product acetic acid, or one of more intermediate of recycle streams of the process may be contacted with one or more absorbent, adsorbent, or ion exchange resins, collectively referred to herein as purification resins. The acetic acid is contacted within a resin bed or guard column 200 to remove various impurities to produce the final acetic acid product.

Impurities removed by the purification resins may include alkyl iodides. In particular, alkyl iodides comprises from 1 to about 20 carbon atoms. Other impurities include various corrosion metals such as chromium, nickel, iron, and the like.

Suitable purification resins for purposes herein include macro reticulated, strong acid cationic exchange resins with at least one percent of their active sites converted to the silver or mercury form. The amount of silver or mercury associated with the resin may be from 1 to 100% of the active sites of the resin, or about 25 percent to about 75 percent, or at least about 50 percent of the active sites may be converted to the silver or mercury form (cf. U.S. Pat. No. 4,615,806, the contents of which are fully incorporated by reference herein). Other suitable examples include U.S. Pat. No. 5,139,981, which is directed to removing iodides from liquid carboxylic acid contaminated with a halide impurity by contacting the liquid halide contaminant acid with a silver (I) exchanged macroreticular resin. Suitable examples of purification resins include Amberlyst® 15 resin (Rohm and Haas), zeolite cationic ion exchange substrates (cf. U.S. Pat. No. 5,962,73), and the like. Other suitable purification resins and methods include those disclosed in U.S. Pat. Nos. 5,227,524, 5,801,279, 5,220,058, EP0685445, and U.S. Pat. No. 6,657,078, the contents of which are fully incorporated by reference herein.

In embodiments, the acetic acid is contacted with the purification resin at a temperature of at least about 50° C., or about 60° C. to about 100° C., or at temperatures greater than or equal to about 150° C. depending on the type of purification resin employed.

In embodiments, the flow rate of acetic acid through the column may be from about 0.5 to about 20 bed volumes per hour (BV/hr), wherein a bed volume is defined as the volume occupied by the resin in the bed. In embodiments, the flow rate may be from about 6 to about 10 BV/hr, or about 7 to 8 BV/hr.

In embodiments, the column may comprise an anionic guard bed, comprising a pyridine or pyrrolidone resin. The terminology "pyridine resin", "pyridine ring-containing polymer", "pyridine polymer" and the like used herein refer to a polymer containing substituted or non-substituted pyridine rings or substituted or non-substituted, pyridine-containing polycondensed rings such as quinoline rings. In embodiments, the resins may comprise a high degree of crosslinking, i.e., greater than 10 wt %. The substituents include those inert to the methanol carbonylation process conditions such as an alkyl group and alkoxy group. Suitable examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of styrene, vinylbenzene and divinylbenzene, copolymers of vinylmethylpyridine and divinylbenzene and copolymers of vinylpyridine, methyl acrylate and ethyl diacrylate (cf. U.S. Pat. No. 5,334,755, the disclosure of which is incorporated herein by reference).

Suitable "pyrrolidone resin", "pyrrolidone ring-containing polymer", pyrrolidone polymer and the like include polymers containing substituted or non-substituted pyrrolidone rings. The substituents may include those inert to the methanol carbonylation medium such as alkyl groups or alkoxy groups. Examples of insoluble, pyrrolidone ring-containing polymer include those obtained by reaction of vinyl pyrrolidone with a di-vinyl monomer-containing vinyl monomer such as a co-polymer of a vinyl pyrrolidone and divinyl benzene. Suitable examples of pyrrolidone polymers include those disclosed in U.S. Pat. Nos. 5,466,874, 5,286,826, 4,786,699, 4,139,688, the disclosures of which are incorporated herein by reference, and those available under the trade name of Reillex® from Reilley Tar and Chemical Corporation of Indianapolis, USA.

In embodiments, the nitrogen heterocyclic ring-containing polymer may be crosslinked by at least 10%, or at least 15% or 20%, and less than 50%, or 60%, or 75% to provide mechanical strength, wherein the "degree of crosslinking" refers to the content, in terms of % by weight, of the divinyl monomer or other crosslinking moiety.

In embodiments, suitable pyridine or pyrrolidone insoluble polymers include free base forms, and/or N-oxide forms, and/or quaternized forms. In embodiments, the insoluble, pyridine or pyrrolidone ring-containing polymer may be in a bead or granular form, or a spherical form, having a particle diameter of 0.01-2 mm, or 0.1-1 mm, or 0.25-0.7 mm. Commercially available pyridine-containing polymers include Reillex-425 (Reilly Tar and Chemical Corporation), KEX-316, KeX-501 and KEX-212 (products of Koei Chemical Co., Ltd.), and the like.

In embodiments, product acetic acid is withdrawn from drying column 130 at or near the bottom of the column via stream 146 and contacted with one or more resins in column comprising the purification resin. As used herein, the column comprising the purification resin may be referred to as a purification column, as a guard bed assembly or column, or simply as a column. These terms are used interchangeably herein. The purification or guard bed assembly is generally represented in FIG. 1 as 200.

Figure 2:
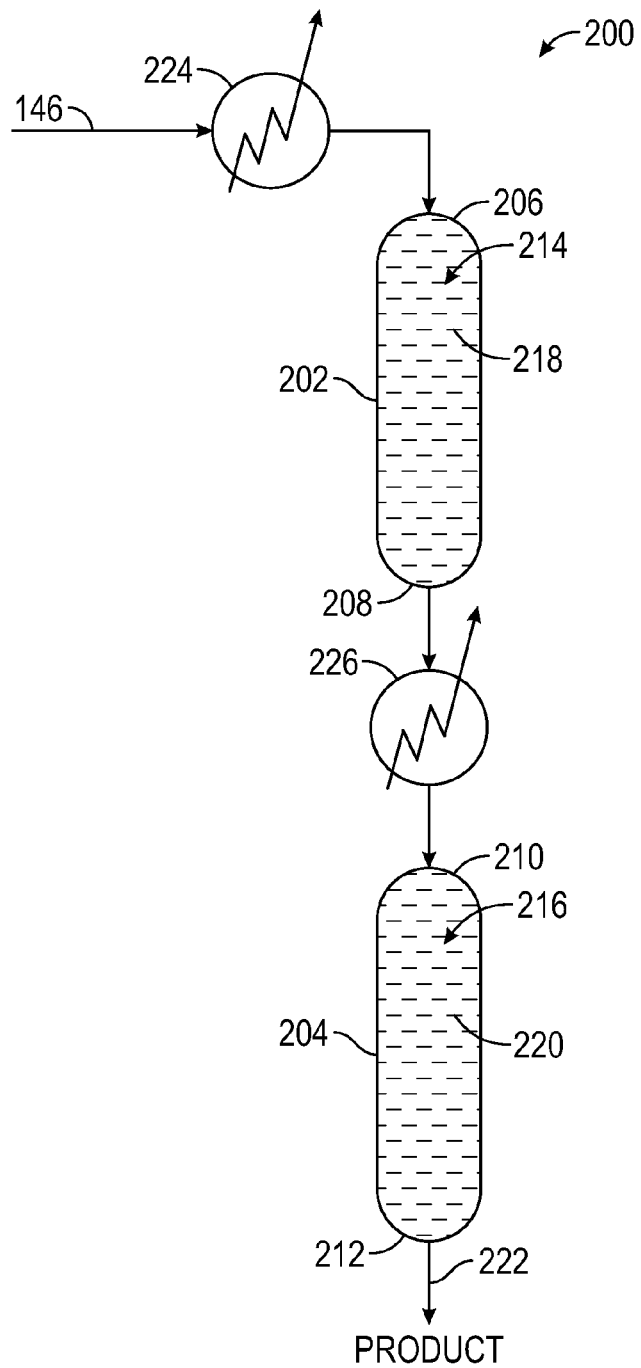
FIG. 2 is a schematic diagram of a series of treatment devices according to an embodiment.

In embodiments, as shown in FIG. 2, the guard bed assembly 200 may comprise one or more treatment devices, e.g., column 202, and column 204, each comprising an inlet end 206 and 210, respectively, and an outlet end 208 and 212, respectively. The inlets are separated from the outlets by an inner chamber 214 and 216. An amount of the purification resin 218 and 220 is located within the inner chamber.

The acetic acid from the process, having an impurity at a first concentration 146 is directed through the inner chamber 214 and 216 in contact with the purification resin 218 and 220 at a temperature and flow rate sufficient to produce a purified acetic acid stream 222 in which the impurity is present, if at all, at a second concentration which is less than the first impurity concentration. Accordingly, the second concentration of the impurity may be zero or otherwise non-detectable.

In embodiments, the guard bed assembly may further comprise heat exchangers 224 and 226, which control the temperature at which the acetic acid contacts the purification resin. In embodiments, the columns 202 and 204 are plug flow columns, which flow downhill with gravity from top to the bottom. However, a device which flows against gravity from a bottom inlet end to a top outlet end is also contemplated.

In embodiments, a first column 202 may comprise an outlet end 208 in direct fluid communication with an inlet end 210 of a second column 204. In embodiments, the conduits between the various devices may be arranged such that any one of a plurality of the columns may be the first treatment device, and any of the remaining columns may be subsequently disposed in series. In embodiments, a plurality of columns may be arranged in a parallel configuration.

In embodiments, the purification resin 218 of the first column 202 may be different than the purification resin 220 in the second column 204, and/or the temperature of the first column 202 may be different than the temperature of the second column 204, and/or a volume of the inner chamber 214 of the first column 202 may be different than a volume of the inner chamber 216 of the second column 204.

Figure 3:
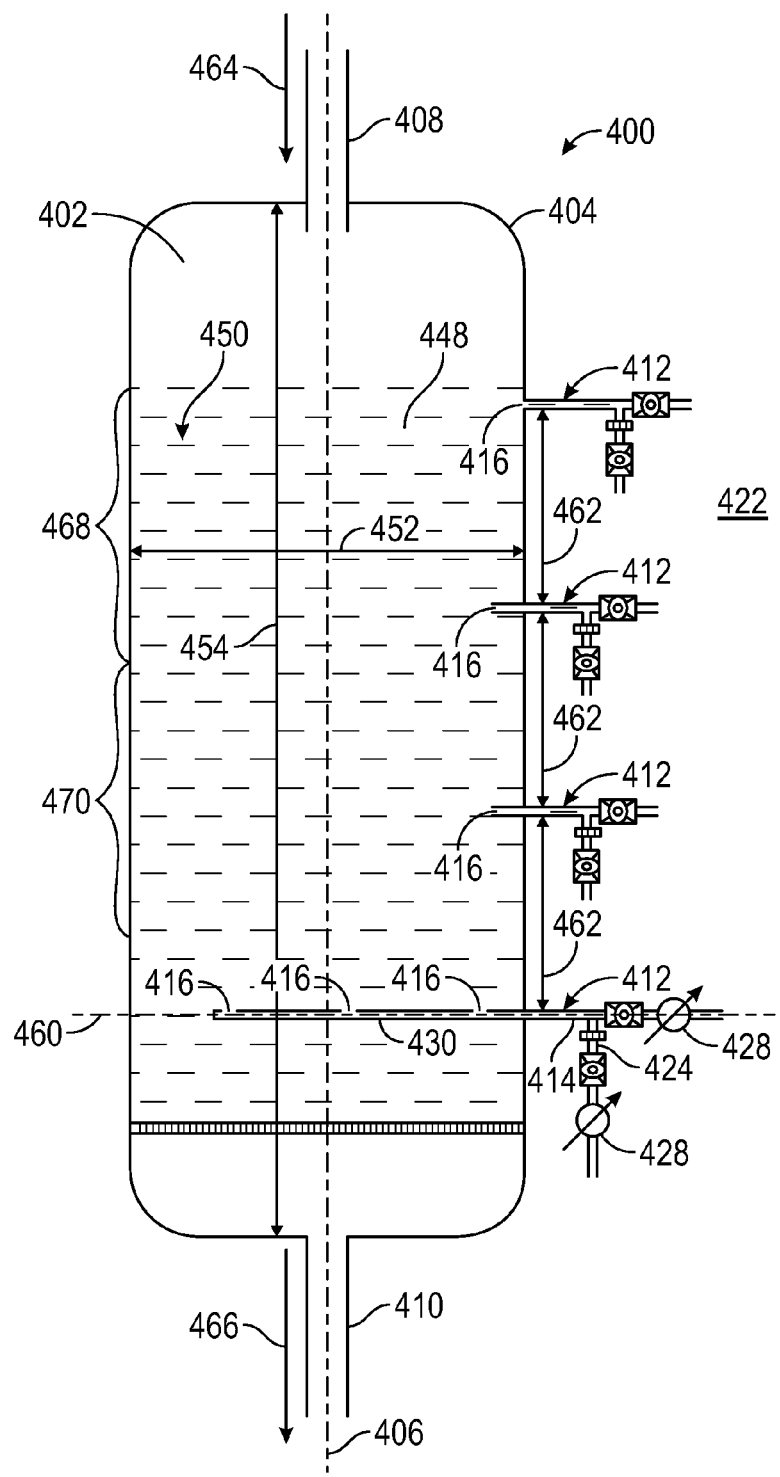
FIG. 3 is a cross-sectional view of a treatment device according to an embodiment.

As shown in FIG. 3, in embodiments, the column 400 comprises an inner chamber 402 bound by a plurality of sides 404 radially arranged about a central axis 406. In embodiments, the column 400 comprises an infinite number of sides, i.e., has a circular cross-section. The column 400 further comprises an inlet end 408 in fluid communication with, and longitudinally separated from, an outlet end 410 through the inner chamber 402. In embodiments, column 400 further comprises a plurality of sampling ports 412 disposed through at least one of the sides 404. The sampling ports may be solid sampling ports, liquid sampling ports, or a combination thereof.

Figure 4:
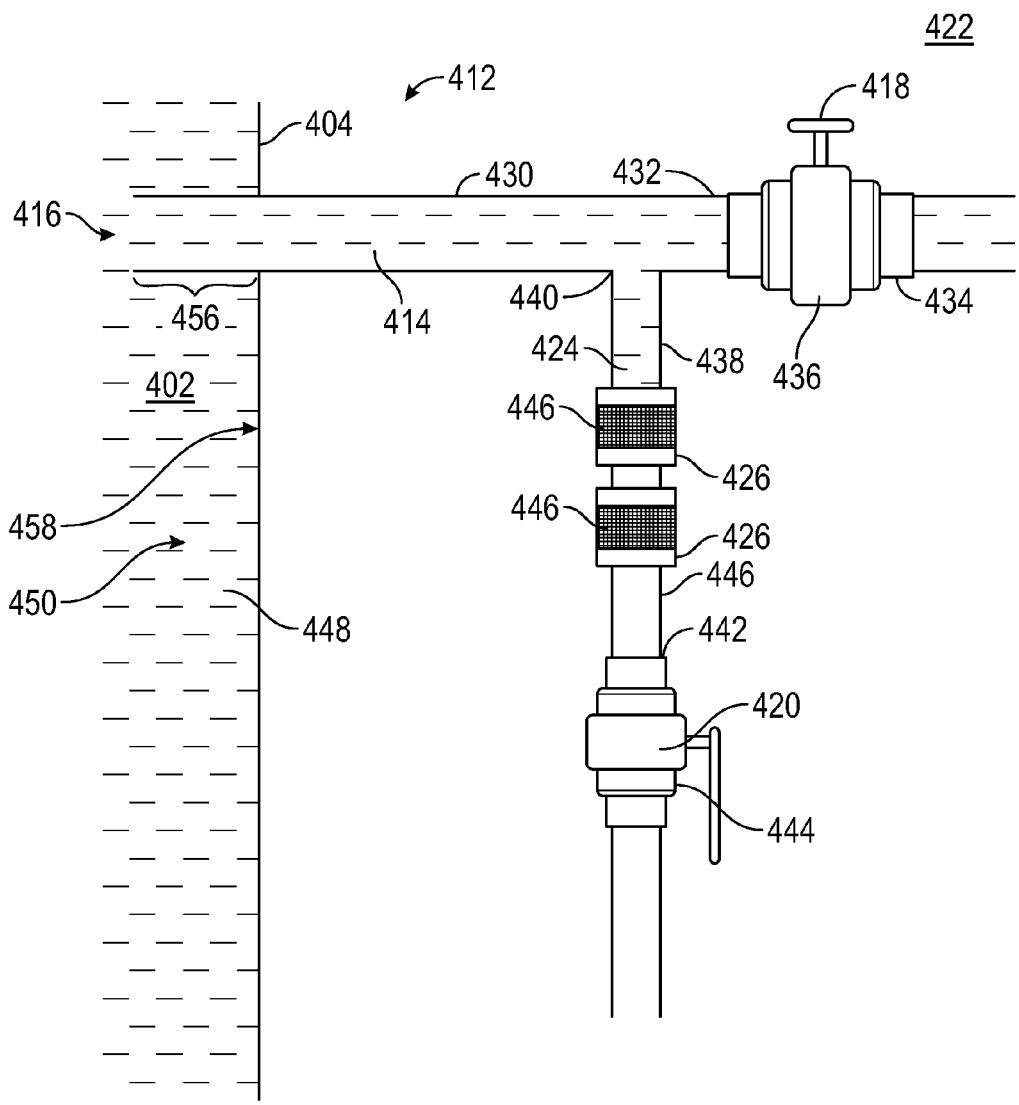
FIG. 4 is a cross-sectional view of a sampling device according to an embodiment.

As shown in FIG. 4, in embodiments, each sample port 412 comprises a first open flow path 414 between a sample inlet 416 located within the inner chamber 402 and a first flow control element 418 operable between an open position (as shown in flow control element 420, e.g., a ball of a ball valve), and a closed position (as shown in flow control element 418), the flow control element being located external to the inner chamber 402, in an external environment 422. The term "open flow path" refers to a flow path dimensioned and arranged to allow both liquid and solid matter to pass through it. Accordingly, the relative size of the open flow path must be determined relative to the average particle size of the solid or semi-solid material which will pass there-through.

When the flow control element is in the open position, there exists fluid communication between the inner chamber 402 and the external environment 422. In embodiments, the first flow path 414 and the second flow path 424 are each in fluid communication with an external environment 422 when the corresponding flow control element 418 and 420, respectively, is in the open position. When the flow control element is in the closed position, fluid communication between the inner chamber 402 and the external environment 422 is prevented.

In embodiments, the sample port further comprises a second flow path 424 comprising a porous element 426 disposed between the sample inlet 416 and a second flow control element 420 operable between an open position and a closed position located external to the inner chamber 402.

In embodiments, the second flow path 424 comprises a portion of the first flow path 414 between the sample inlet 416 and the first flow control element 418. Accordingly, in embodiments, the second flow path may be in a "T-plan" or "Y-plan" orientation off of the first flow path such that a sample exiting through the first control element 418 is taken from the same place in the inner chamber 402 as a sample exiting through the second flow control element 420.

In embodiments, as shown in FIG. 3, the first flow path 414, the second flow path 424, or both, further comprise a heat exchanger 428 located between the sample inlet 416 and the external environment 422. In embodiments, the heat exchanger 428 may be removably attached to a portion of the flow path past the flow control element as shown. Accordingly, the heat exchanger 428, also referred to as a "sample cooler", i.e., a piece of cooled tubing in a bucket of ice water, may be utilized to acquire samples of the inner chamber 402, when the inner chamber is at an elevated temperature.

In embodiments, the first flow path 414 is located within a first conduit 430 having a first outlet end 432 equipped with a first valve 434 comprising the first flow control element 418. In embodiments, the valve may be a ball valve, a gate valve, and/or the like. In embodiments, the first valve is a severe service ball valve equipped with a seat flush system 436 to prevent particulate matter, e.g., the ion exchange resin located in inner chamber 402, from inhibiting closing of the valve after a sample is obtained.

In embodiments, the second flow path 424 is at least partially located within a second conduit 438 attached at an attachment point 440 to the first conduit 430, and having a second outlet end 442 equipped with a second valve 444 comprising the second flow control element 420. In embodiments, the porous element 426 is located at or proximate to the attachment point 440, at or proximate to the second outlet end 442, or a combination thereof. In embodiments, the porous element comprises a screen, a porous frit, a filter element, or a combination thereof, generally represented as 446. In embodiments, when a plurality of porous elements is utilized, the exclusion size of the element may be varied. For example, in embodiments, the screen or filter element 446 of the porous element 426 may be a 100 mesh screen in a first position, and a 200 mesh screen in a second downstream position, depending on the relative size of the particulate matter (e.g., the purification resin) contained within inner chamber 402.

In embodiments, the first open flow path 414 is dimensioned and arranged to allow both liquid 450 and solids 448 from the inner chamber 402 to flow from the sample inlet 416 through the first flow control element 418 in the open position, and into an external environment 422; and the second flow path 424 is dimensioned and arranged to allow the liquid 450 present in the inner chamber 402 to flow from the sample inlet 416 through the porous element 426, through the second flow control element 420 in the open position, and into the external environment 422, while excluding at least a portion of solids or semisolid material 448 present in the inner chamber 402 from flowing through the second flow control element 420.

In embodiments, at least a portion 456 of the first flow path 414 is located within a first conduit 430 extending into the inner chamber 402 away from an inner surface 458 of the side 404 through which the sampling port 412 is disposed, such that the sample inlet 416 is located within the inner chamber 402 spaced away from the side 404.

As shown in FIG. 3, in embodiments, the sample inlet 416 is located at the side 404 through which the sampling port 412 is disposed.

In embodiments, the inner chamber 402 has an average inner diameter 452 determined orthogonal to the central axis 406 between opposing sides 404 which is less than 50% of an average length 454 of the inner chamber 402 determined parallel to the central axis 406 between the inlet end 408 and the outlet end 406. In embodiments, the first conduit 430 comprises a plurality of sample inlets 416. In embodiments, all of the plurality of sample inlets of a single first conduit 430 are located coplanar with a plane 460 orthogonal to the central axis 406.

In embodiments, the sampling ports 412 are arranged longitudinally (along at least a portion of one or more sides parallel to the central axis from the inlet 408 end to the outlet end 410) at essentially equal intervals 462 along at least a portion of the side 404.

In embodiments, a process comprise providing a column 400 according to any one or combination of embodiments disclosed herein comprising at least one, preferably a plurality of sampling ports 412 according to any one or combination of embodiments disclosed herein wherein the inner chamber 402 comprises an amount of a purification resin 448 at least partially filling the inner chamber 402. The stream to be purified 464, e.g., an acetic acid stream and/or an intermediate production stream, having one or more impurities at a first concentration is then directed through the column from the inlet end 408 through the inner chamber 402 contacting the purification resin 448 then through the outlet end 410 at a temperature and flow rate sufficient to produce a purified liquid stream 466, e.g., a purified acetic acid stream and/or an intermediate production stream, having an impurity at a second concentration which is less than the first concentration.

In embodiments, the purification resin 448 comprises a macroreticular, strong acid, ion exchange resin wherein at least about 1 percent of the active sites of the resin have been converted to the silver or mercury form; wherein the temperature is at least about 50° C., and wherein the silver or mercury exchanged ion exchange resin is effective to remove at least about 90 percent by weight of $C_1$-$C_{20}$ organic iodides in the acetic acid stream.

In embodiments, the purification resin 448 is present within the inner chamber 402 in a plurality of bands 468 and 470, a first band 468 located between the inlet end 408 and the second band 470, and the second band 470 located between the first band 468 and the outlet end 410. In embodiments, the purification resin in the first band 468 is the same as the purification resin in the second band 470. In alternative embodiments, the purification resin in the first band 468 is different than the purification resin in the second band 470. In embodiments, the purification resin in the first band 468 is a non-functionalized macroreticular, strong acid, ion exchange resin and the purification resin in the second band 470 comprises a macroreticular, strong acid, ion exchange resin wherein at least about 1 percent of the active sites of the resin have been converted to the silver or mercury form.

In embodiments, a process according to one or more embodiments disclosed herein further comprises operating a first flow control element 418 from a closed positon to an open position for a period of time sufficient to obtain a sample comprising liquid 450 and purification resin 448 from a first sampling port and then returning the first flow control element 418 back to a closed position, and/or operating a second flow control element 420 from a closed positon to an open position for a period of time sufficient to obtain a sample comprising liquid 450 from a first sampling port and then returning the second flow control element 420 back to the closed position.

In embodiments, the process may further comprise analyzing one or more of the samples to determine one or more concentrations of one or more impurities at the corresponding sampling port. In embodiments, the process may further comprise attaching a heat exchanger to an outlet of the sampling port prior to operating the valve to obtain a sample having a reduced temperature relative to the temperature of the inner chamber. In embodiments, the process may further comprise providing a plurality of the columns wherein an outlet end of a first column is in direct fluid communication with an inlet end of a second column.

Operation and Monitoring of the Purification Column

In embodiments, samples obtained from the sampling ports may include a sample of the purification resin present in the column, a liquid sample of the acetic acid stream present in the column, or both. The arrangement of the sampling ports allows for samples to be obtained at discrete points through the resin bed.

A sampling port may also be located proximate to the final purified acetic acid stream produced by the column.

Determination of the impurity levels present in a sample will necessarily depend on the type of sample being analyzed. Liquid samples may be amenable to gas chromatographic (GC) analysis, high pressure liquid chromatography (HPLC) analysis, which is to be understood to include normal phase, reverse phase, ion exclusion, ion pair, size exclusion, ion exchange, and ion chromatographic techniques readily understood by one having minimal skill in the art. Any form of suitable detector may be employed. Likewise, resin samples may be extracted and/or digested to allow for any of the various chromatographic techniques, and/or may be analyzed via wet chemical techniques, atomic absorption analysis, which may include inductively coupled plasma (ICP) analysis, mass spectral analysis, ICP-MS and/or the like. In an embodiment, the resin samples may be analyzed using X-ray fluorescence techniques, as are readily understood by one of minimal skill in the art.

In embodiments, the samples may be analyzed for halogens, or iodide (I) and/or for various transition metals from Groups 3 to 12, or corrosion metals typical of acetic acid production such as Fe, Cr, and/or Ni, and may also be analyzed for the presence of the metal or moiety with which the active sites of the resin were converted, which may include silver and/or mercury.

In embodiments, a combination of utilizing the sampling ports and analysis may be used to control column operation, which may include monitoring the ability of the column to remove impurities and diverting flow around the column prior to the impurity retention or removal characteristics of the column being exhausted.

In embodiments, an impurity concentration of a sample may be compared a previously determined impurity concentration value which indicates whether or not the purification resin is functioning or has become exhausted. This information may be combined with the location of the sample port such that the impurity concentration of the sample indicates exhaustion of the purification resin at a point in the column corresponding to the location of the sample port from which the sample was obtained.

In embodiments, a resin is exhausted when it is in longer capable of purifying the acetic acid to an acceptable level. In embodiments, a purification resin is considered "exhausted" when the acetic acid which has contacted this resin has an iodide concentration above 100 ppb by weight, a Fe, Cr, and/or Ni concentration above 500 ppb by weight, or a combination thereof.

In addition, in embodiments, a resin sample containing greater than or equal to about 10 weight percent of the impurity is also considered to be exhausted for purposes herein. However, it is to be understood that these levels merely reflect current requirements for product acetic acid, and any such levels may be used. Furthermore, the levels used and the impurities analyzed for (determined) may be different than iodide and corrosion metals, depending of the stream in which the column is placed.

In embodiments, an indication of an exhausted column, as determined by a final purified acetic acid sample which has an impurity profile above an acceptable level, may result in flow through the particular column being stopped and/or diverted though a suitable column.

In embodiments, the progression of the impurities through the column may be used to determine the rate at which the column is becoming exhausted, and thus may be used to predict the life expectancy or otherwise control the use of the column in the process In an embodiment, a determination of exhausted resin proximate to the end of the column, but not yet in the final purified acetic acid, may be utilized to stop or otherwise divert flow around the column to allow for resin replacement and/or resin regeneration.

In embodiments, once the flow of acetic acid through the column is stopped, the resin may be regenerated. In embodiments, the regeneration of the exhausted resin comprises removing at least a portion of the exhausted resin from the column and refilling at least a portion of the column with active purification resin. In embodiments, at least a portion of the active resin used to refill the column comprises previously exhausted resin which has been regenerated into active purification resin. In embodiments, at least a portion of the exhausted resin is regenerated into the active purification resin within the column, also referred to as in-situ regeneration. Regeneration of the resin depends on the type of resin and the impurities being removed. Regeneration processes may include contacting the resin with suitable solvents, reagents, and/or the like.

Charging a Column with Resin

Figure 5:
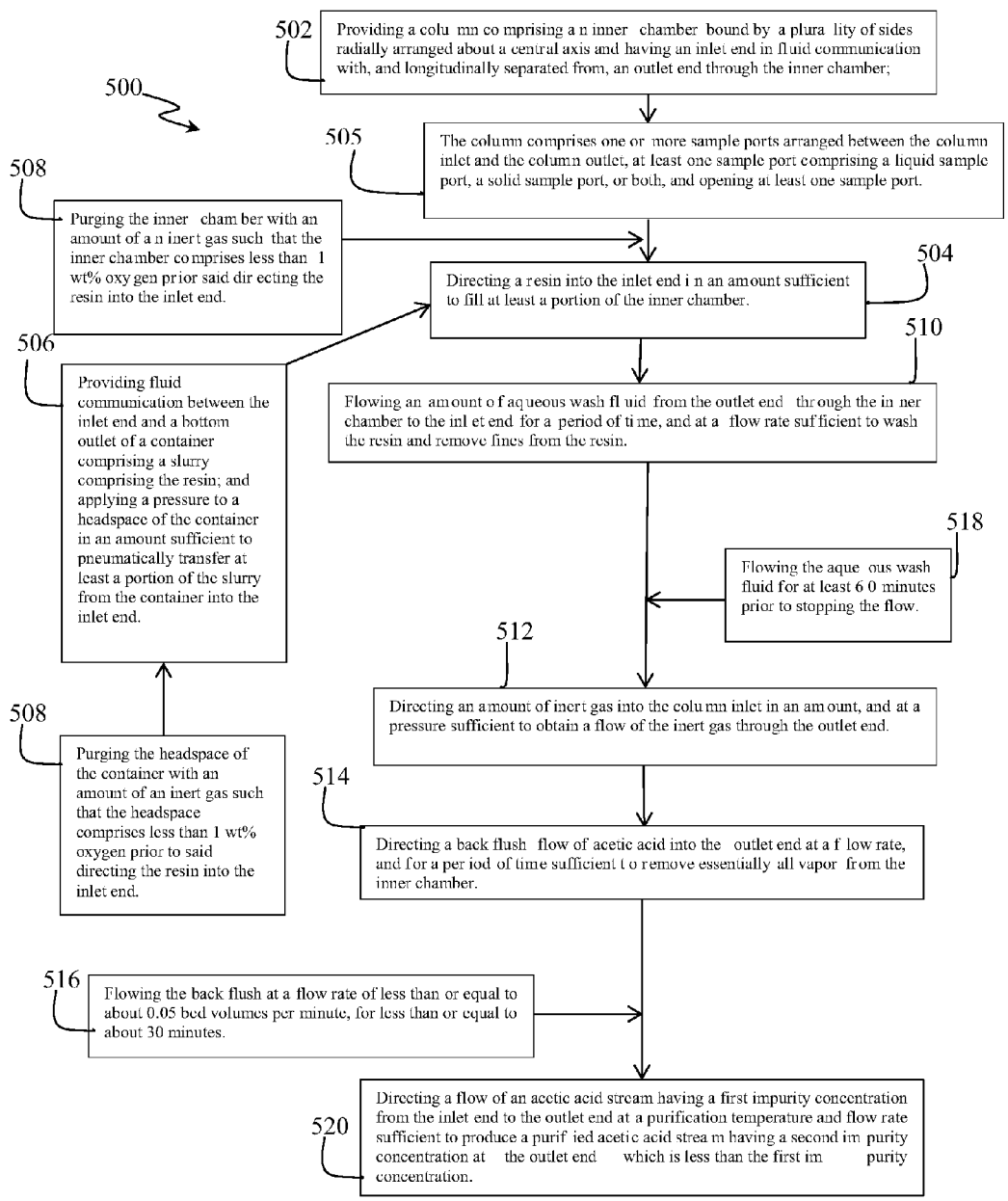
FIG. 5 is a block diagram showing the step for charging a treatment device column with resin according to embodiments.

As shown in FIG. 5, in embodiments, a method or process 500 comprises the steps of providing a column according to any one or combination of embodiments disclosed herein comprising an inner chamber 502. The process may further include a column comprising one or more sample ports arranged between the column inlet and the column outlet, at least one sample port comprising a liquid sample port, a solid sample port, or both, and opening at least one sample port 505.

Next the method or process includes directing an amount of purification resin into the inner chamber sufficient to fill a portion of the inner chamber 504. In embodiments, filling the column comprises opening at least one sample port. In embodiments, the sample ports may be used to wash the resin, to remove vapor from the resin, to purge the inner chamber with inert gas during charging of the resin, and/or the like.

In embodiments, the resin may be place into the column in a dry or wet form by either manually transferring the resin into the top of the column or pumping a slurry into the column. In embodiments, the resin may be supplied as a slurry in a container, such as liquid tote, a tank truck, or tanker rail car, and pneumatically transferred into the column. Accordingly, in embodiments, a bottom outlet of a container comprising a slurry comprising the purification resin is put into fluid communication with the inner chamber. A pressure is then applied to a headspace of the container in an amount sufficient to pneumatically transfer at least a portion of the slurry from the container into the inner chamber 506.

In embodiments, after pneumatically transferring the resin into the column by pumping or by pressuring the container, additional water or other solvent may be added to the container and the transfer processes repeated to ensure essentially all of the resin has been transferred. Prior to and/or during transfer of the resin, in embodiments the column and/or the containers are purged with nitrogen or another inert gas to remove oxygen 508.

In embodiments, the resin may then be backwashed 510 with a wash fluid, typically water or another solvent to remove fines, foreign matter, and artifacts of production. The wash may persist for at least 60 minutes 518. This backwash may be sent to waste or otherwise recycled as may be appropriate. Washing times may be an hour or more, at relatively high flow rates to ensure even dispersion of the resin within the column and to prevent pockets in the resin. The wash may then be removed from the resin by applying pressure to the top of the column 512 using nitrogen or the like, and maintaining the pressure until the gas blows through the column outlet, indicating that essentially all of the wash has been removed.

The resin may then once again be back flushed only this time with acetic acid 514. In embodiments, the acid back flush is conducted at a relatively slow rate, with a flow rate of acid into the base of the column of less than 0.05 or less than 0.04 bed volumes per minute 516. The back flush may be conducted until all of the vapor present within the column has been displaced by liquid. In embodiments, at least some of the vapor is removed through one or more open sample ports. In embodiments, only a portion of the inner chamber is initially filled with resin to allow for swelling of the resin, which in embodiments may be as much as 40% or more when the resin is exchanged from water to acetic acid.

Once the resin is backwashed, the column may be put into use by directing the flow of acetic acid having the first impurity concentration from the inlet end to the outlet end at a purification temperature and flow rate sufficient to produce a purified acetic acid stream having a second impurity concentration at the outlet end which is less than the first impurity concentration 520.

As is evident from the figures and text presented above, a variety of embodiments are contemplated:

E1. A process, comprising:
  a) providing a treatment device column comprising an inner chamber comprising an active purification resin located between a column inlet and a column outlet, the column further comprising one or more sample ports arranged between the column inlet and the column outlet, at least one sample port comprising a liquid sample port, a solid sample port, or both; and
  b) flowing an acetic acid stream having a first concentration of an impurity through the column at a temperature and flow rate sufficient to produce a purified acetic acid stream at the column outlet having a second concentration of the impurity, if any, which is less than the first concentration.

E2. The process according to embodiment E1, further comprising opening at least one sample port.

E3. The process according to embodiment E1 or E2, wherein the impurity comprises iodine, chromium, nickel, iron, or a combination thereof.

E4. The process according to any one of embodiments E1 to E3, wherein the purification resin comprises a macroreticular, strong acid, ion exchange resin having at least about 1 percent active sites in a silver or mercury form.

E5. The process according to any one of embodiments E1 to E4, wherein the temperature is at least about 50° C.

E6. The process according to any one of embodiments E1 to E5, further comprising obtaining a sample of the purification resin through at least one solid sample port, a liquid sample of the acetic acid stream present in the column through at least one liquid sample port, or a combination thereof, and determining a concentration of the impurity in at least one sample.

E7. The process according to embodiment E6, wherein the concentration of the impurity is determined using gas chromatography, high pressure liquid chromatograph, atomic absorption, inductively coupled plasma spectroscopy, mass spectroscopy, x-ray fluorescence spectroscopy, or a combination thereof.

E8. The process according to embodiment E6 or E7, further comprising comparing the impurity concentration of at least one sample to a previously determined impurity concentration value, and determining if the impurity concentration of the sample indicates exhaustion of the purification resin at a point in the column corresponding to the location of the sample port from which the sample was obtained.

E9. The process according to any one of embodiments E1 to E8, further comprising stopping the flow of acetic acid through the column.

E10. The process according to any one of embodiments E1 to E9, wherein the flow of acetic acid is stopped prior to exhaustion of essentially all of the active purification resin present in the column.

E11. The process according to any one of embodiments E1 to E10, further comprising providing a second column comprising an inner chamber comprising an active purification resin located between a second column inlet and a second column outlet, and flowing the acetic acid stream having the first concentration of the impurity through the second column at a temperature and flow rate sufficient to produce the purified acetic acid stream at the second column outlet having the second concentration of the impurity, if any, which is less than the first concentration.

E12. The process according to any one of embodiments E1 to E11, further comprising regenerating at least a portion of the exhausted resin and resuming flow of the acetic acid stream through the column to produce the purified acetic acid stream.

E13. The process according to embodiment E12 wherein the regeneration of the exhausted resin comprises removing at least a portion of the exhausted resin from the column and refilling at least a portion of the column with active purification resin.

E14. The process according to embodiment E12 or E13 wherein at least a portion of the active resin used to refill the column comprises previously exhausted resin which has been regenerated into active purification resin.

E15. The process according to any one of embodiments E12 to E14 wherein at least a portion of the exhausted resin is regenerated into the active purification resin within the column.

E16. A process comprising:
  a. providing a treatment device column comprising an inner chamber bound by a plurality of sides radially arranged about a central axis and having an inlet end in fluid communication with, and longitudinally separated from, an outlet end through the inner chamber;

b. directing an amount of purification resin into the inner chamber sufficient to fill a portion of the inner chamber;

c. flowing an aqueous wash fluid from the outlet end through the inner chamber to the inlet end at a flow rate and for a period of time sufficient to wash and/or remove fines from the purification resin; and d. flowing an acetic acid stream having a first concentration of an impurity through the column at a temperature and flow rate sufficient to produce a purified acetic acid stream at the column outlet having a second concentration of the impurity, if any, which is less than the first concentration.

E17. The process according to embodiment E16, wherein the column comprises one or more sample ports arranged between the column inlet and the column outlet, at least one sample port comprising a liquid sample port, a solid sample port, or both, and the process further comprises opening at least one sample port.

E18. The process according to embodiment E16 or E17, wherein the aqueous wash fluid is flowed for at least 60 minutes.

E19. The process according to any one of embodiments E16 to E18, further comprising directing an amount of inert gas into the column inlet in an amount, and at a pressure sufficient to obtain a flow of the inert gas through the outlet end after step (c).

E20. The process according to any one of embodiments E16 to E19, further comprising directing a back flush flow of acetic acid into the outlet end at a flow rate, and for a period of time sufficient to remove essentially all vapor from the inner chamber.

E21. The process according to embodiment E20, wherein the flow rate of the back flush flow of acetic acid is less than or equal to about 0.05 bed volumes per minute, and the period of time is less than or equal to about 30 minutes.

E22. The process according to any one of embodiments E16 to E21, wherein said directing the purification resin into the inner chamber comprises providing fluid communication between the inner chamber and a bottom outlet of a container comprising a slurry comprising the purification resin; and applying a pressure to a headspace of the container in an amount sufficient to pneumatically transfer at least a portion of the slurry from the container into the inner chamber.

E23. The process according to any one of embodiments E16 to E22, further comprising purging the inner chamber, the headspace of the container, or both with an amount of an inert gas such that the inner chamber and/or the headspace comprises less than 1 wt % oxygen prior to said directing the purification resin into the inner chamber.

E24. The process according to any one of embodiments E16 to E23, wherein the impurity comprises iodine, chromium, nickel, iron, or a combination thereof; wherein the purification resin comprises a macroreticular, strong acid, ion exchange resin having at least about 1 percent active sites in a silver or mercury form; wherein the temperature is at least about 50° C., or a combination thereof.

E25. The process according to any one of embodiments E16 to E23, wherein the impurity comprises iodine, chromium, nickel, iron, or a combination thereof; wherein the purification resin comprises a macroreticular, strong acid, ion exchange resin having at least about 1 percent active sites in a silver or mercury form; wherein the temperature is at least about 50° C., or a combination thereof.

E26. The process according to any one of embodiments E1 to E15, wherein the providing of the column comprising an inner chamber comprising an active purification resin located between a column inlet and a column outlet, is according to any one of embodiments E16 to E25.

E27. A process comprising carbonylating at least one member selected from the group consisting of methanol, dimethyl ether, and methyl acetate in the presence of 0.1 to less than 14 wt. % water, a rhodium catalyst, methyl iodide and lithium iodide, to form a reaction medium comprising acetic acid in a reactor;

separating the reaction medium into a liquid recycle stream and a vapor product stream;

separating the vapor product stream in up to 2 distillation columns in a primary purification train to produce a crude acid product comprising acetic acid comprising lithium cations;

contacting the crude acetic acid product with a cationic exchanger in the acid form within a first treatment device to produce an intermediate acid product; and contacting the intermediate acetic acid product with a metal-exchanged ion exchange resin having acid cation exchange sites within a second treatment device to produce a purified acetic acid, wherein the contact within the first treatment device, the second treatment device, or both is according to any one of embodiments E1 to E15.

E28. A process comprising: carbonylating at least one member selected from the group consisting of methanol, dimethyl ether, and methyl acetate in the presence of 0.1 to less than 14 wt. % water, a rhodium catalyst, methyl iodide and lithium iodide, to form a reaction medium comprising acetic acid in a reactor;

separating the reaction medium into a liquid recycle stream and a vapor product stream;

separating the vapor product stream in up to 2 distillation columns in a primary purification train to produce a crude acid product comprising acetic acid comprising lithium cations;

contacting the crude acetic acid product with a first purification resin comprising a cationic exchanger in the acid form within a first treatment device to produce an intermediate acid product; and contacting the intermediate acetic acid product with a second purification resin comprising a metal-exchanged ion exchange resin having acid cation exchange sites within a second treatment device to produce a purified acetic acid stream, the first treatment device, the second treatment device, or both individually comprising at least one sampling port disposed through a side of the treatment device;

obtaining a sample of the first purification resin, the second purification resin, a liquid sample of the acetic acid stream present in the treatment device, or a combination thereof through the corresponding sample port; and determining a concentration of an impurity in at least one sample.

E29. The process according to embodiment E27 or E28, further comprising comparing the impurity concentration of at least one sample to a previously determined impurity concentration value, and determining if the impurity concentration of the sample indicates exhaustion of the purification resin at a point in the treatment device corresponding to the location of the sample port from which the sample was obtained.

E30. The process according to any one of embodiments E27 to E29, further comprising stopping the flow of acetic acid through the treatment device prior to exhaustion of essentially all of the active purification resin present in the treatment device, regenerating at least a portion of the exhausted resin according to any one of embodiments E16 to E26, and resuming flow of the acetic acid stream through the treatment device to produce the purified acetic acid stream.

E31. The process according to any one of embodiments E27 to E30, wherein the metal-exchanged ion exchange resin comprises at least 1% strong acid exchange sites occupied by silver.

E32. The process according to any one of embodiments E27 to E31, wherein the crude acid product comprises up to 10 ppm lithium.

E33. The process according to any one of embodiments E27 to E32, wherein separating the vapor product stream comprises:
distilling the vapor product stream in a first distillation column and taking a sidedraw to yield a distilled acetic acid product; and
distilling the distilled acetic acid product in a second distillation column to produce a crude acid product comprising acetic acid and lithium cations.

E34. The process according to any one of embodiments E27 to E33, further comprising a step of adding a potassium salt selected from the group consisting of potassium acetate, potassium carbonate, and potassium hydroxide to the distilled acetic acid product prior to distilling the distilled acetic acid product in a second distillation column; wherein at least a portion of the potassium is removed by the cationic exchanger in the acid form.

E35. The process according to any one of embodiments E27 to E34, wherein the crude acetic acid product is contacted with the cationic exchanger at a temperature from 50° C. to 120° C.

E36. The process according to any one of embodiments E27 to E35, wherein the intermediate acetic acid product is contacted with the metal-exchanged ion exchange resin at a temperature from 50° C. to 85° C.; or a combination thereof.

E37. The process according to any one of embodiments E27 to E36, wherein the intermediate acetic acid product has a lithium ion concentration of less than 50 ppb.

E38. The process according to any one of embodiments E27 to E37, wherein the cationic exchanger in the acid form comprises a resin of acid-form strong acid cation exchange macroreticular, macroporous or mesoporous resins.

E39. The process according to any one of embodiments E27 to E38, further comprising treating the purified acetic acid product with a cationic exchange resin to recover any silver, mercury, palladium or rhodium.

E40. The process according to any one of embodiments E27 to E39, wherein the water concentration in the reaction medium is controlled from 0.1 to 5 wt %, based on the total amount of reaction medium present.

E41. The process according to any one of embodiments E27 to E40, further comprising introducing a lithium compound selected from the group consisting of lithium acetate, lithium carboxylates, lithium carbonates, lithium hydroxide, and mixtures thereof into the reactor to maintain the concentration of lithium acetate from 0.3 to 0.7 wt % in the reaction medium.

E42. The process according to embodiment E41, further comprising:
maintaining the hydrogen iodide concentration from 0.1 to 1.3 wt % in the reaction medium;
maintaining the rhodium catalyst concentration from 300 and 3000 wppm in the reaction medium;
maintaining the water concentration from 0.1 to 4.1 wt % in the reaction medium;
maintaining the methyl acetate concentration from 0.6 to 4.1 wt % in the reaction medium; or a combination thereof.

E43. The process according to any one of embodiments E27 to E42, further comprising controlling a butyl acetate concentration in the acetic acid product at 10 wppm or less without directly removing butyl acetate from the acetic acid product.

E44. The process according to embodiment E43, wherein the butyl acetate concentration is controlled by maintaining an acetaldehyde concentration at 1500 ppm or less in the reaction medium.

E45. The process according to embodiment E43 or E44, wherein the butyl acetate concentration is controlled by controlling a temperature in the reactor from 150 to 250° C.

E46. The process according to any one of embodiments E43 to E45, wherein the butyl acetate concentration is controlled by controlling a hydrogen partial pressure in the reactor from 0.3 to 2 atm.

E47. The process according to any one of embodiments E43 to E45, wherein the butyl acetate concentration is controlled by controlling a rhodium catalyst concentration from 100 to 3000 wppm in the reaction medium.

E48. The process according to any one of embodiments E27 to E47, further comprising controlling an ethyl iodide concentration in the reaction medium at less than or equal to 750 wppm.

E49. The process according to embodiment E48, wherein the propionic acid concentration in the product acetic acid is less than 250 wppm, without directly removing propionic acid from the product acetic acid.

E50. The process according to embodiment E48 or E49, wherein ethyl iodide in the reaction medium and propionic acid in the acetic acid product are present in a weight ratio from 3:1 to 1:2;

E51. The process according to any one of embodiments E48 to E50, wherein acetaldehyde and ethyl iodide are present in the reaction medium in a weight ratio from 2:1 to 20:1;

E52. The process according to any one of embodiments E48 to E51, wherein an ethanol concentration in the methanol feed into the reactor is less than 150 wppm; or a combination thereof E53. The process according to any one of embodiments E48 to E52, wherein the ethyl iodide concentration in the reaction medium is controlled by adjusting at least one of a hydrogen partial pressure in the carbonylation reactor, a methyl acetate concentration in the reaction medium, and a methyl iodide concentration in the reaction medium.

While the embodiments have been illustrated and described in detail in the drawings and foregoing description, the same is to be considered as illustrative and not restrictive in character, it being understood that only some embodiments have been shown and described and that all changes and modifications that come within the spirit of the embodiments are desired to be protected. It should be understood that while the use of words such as ideally, desirably, preferable, preferably, preferred, more preferred or exemplary utilized in the description above indicate that the feature so described may be more desirable or characteristic, nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

I claim:

1. A process comprising:
   carbonylating at least one member selected from the group consisting of methanol, dimethyl ether, and methyl acetate in the presence of 0.1 to less than 14 wt. % water, a rhodium catalyst, methyl iodide and lithium iodide, to form a reaction medium comprising acetic acid in a reactor;
   separating the reaction medium into a liquid recycle stream and a vapor product stream;
   separating the vapor product stream in up to 2 distillation columns in a primary purification train to produce a crude acid product comprising acetic acid comprising up to 10 ppm lithium cations;
   contacting the crude acetic acid product with a first purification resin comprising a cationic exchanger in the acid form within a first treatment device to produce an intermediate acid product having a lithium ion concentration of less than 50 ppb; and
   contacting the intermediate acetic acid product with a second purification resin comprising a metal-exchanged ion exchange resin having acid cation exchange sites within a second treatment device to produce a purified acetic acid stream;
   the first treatment device, the second treatment device, or both individually comprising at least one sampling port disposed through a side of the treatment device comprising a first open flow path between a sample inlet located within the treatment device and a first flow control element located external to the treatment device, which is operable between an open and a closed position to obtain a sample of the resin proximate to the sample inlet, and
   a second flow path comprising a porous element disposed between the sample inlet and a second flow control element located external to the treatment device, which is operable between an open and a closed position to obtain a sample of only the liquid proximate to the sample inlet;
   opening the first flow control element to obtain a sample of the purification resin at a point in the treatment device proximate to the sample inlet of the corresponding sample port;
   determining a concentration of an impurity in the sample of the purification resin;
   comparing the impurity concentration of the sample to a previously determined impurity concentration value; and
   determining if the impurity concentration of the sample indicates exhaustion of the purification resin at the point in the treatment device proximate to the sample inlet.

2. The process of claim 1,
   further comprising opening the second flow control element to obtain a sample of only the liquid proximate to the sample inlet;
   determining a concentration of an impurity in the liquid sample;
   comparing the impurity concentration of the liquid sample to a previously determined impurity concentration value, and
   determining if the impurity concentration of the liquid sample indicates exhaustion of the purification resin at a point in the treatment device proximate to the sample inlet.

3. The process of claim 2 further comprising stopping the flow of acetic acid through the treatment device prior to exhaustion of essentially all of the active purification resin present in the treatment device, regenerating at least a portion of the exhausted resin and resuming flow of the acetic acid stream through the treatment device to produce the purified acetic acid stream.

4. The process of claim 1, wherein separating the vapor product stream comprises:
   distilling the vapor product stream in a first distillation column and taking a sidedraw to yield a distilled acetic acid product; and
   distilling the distilled acetic acid product in a second distillation column to produce a crude acid product comprising acetic acid and lithium cations.

5. The process of claim 1, further comprising a step of adding a potassium salt selected from the group consisting of potassium acetate, potassium carbonate, and potassium hydroxide to the distilled acetic acid product prior to distilling the distilled acetic acid product in a second distillation column; wherein at least a portion of the potassium is removed by the cationic exchanger in the acid form.

6. The process of claim 1, wherein the crude acetic acid product is contacted with the cationic exchanger at a temperature from 50° C. to 120° C.

7. The process of claim 1, wherein the intermediate acetic acid product is contacted with the metal-exchanged ion exchange resin at a temperature from 50° C. to 85° C.

8. The process of claim 1, wherein the cationic exchanger in the acid form comprises a resin of acid-form strong acid cation exchange macroreticular, macroporous or mesoporous resins.

9. The process of claim 1, wherein the metal-exchanged ion exchange resin comprises at least 1% strong acid exchange sites occupied by silver.

10. The process of claim 1, further comprising treating the purified acetic acid product with a cationic exchange resin to recover any silver, mercury, palladium or rhodium.

11. The process of claim 1, wherein the water concentration in the reaction medium is controlled from 0.1 to 5 wt %, based on the total amount of reaction medium present.

12. The process of claim 1 further comprising introducing a lithium compound selected from the group consisting of lithium acetate, lithium carboxylates, lithium carbonates, lithium hydroxide, and mixtures thereof into the reactor to maintain the concentration of lithium acetate from 0.3 to 0.7 wt % in the reaction medium.

13. The process of claim 12, further comprising:
   maintaining the hydrogen iodide concentration from 0.1 to 1.3 wt % in the reaction medium;
   maintaining the rhodium catalyst concentration from 300 and 3000 wppm in the reaction medium;
   maintaining the water concentration from 0.1 to 4.1 wt % in the reaction medium;
   maintaining the methyl acetate concentration from 0.6 to 4.1 wt % in the reaction medium; or a combination thereof.

14. The process of claim 1 further comprising controlling a butyl acetate concentration in the acetic acid product at 10 wppm or less without directly removing butyl acetate from the acetic acid product.

15. The process of claim 14, wherein the butyl acetate concentration is controlled by maintaining an acetaldehyde concentration at 1500 ppm or less in the reaction medium;
controlling a temperature in the reactor from 150 to 250° C.;
controlling a hydrogen partial pressure in the reactor from 0.3 to 2 atm;
controlling a rhodium catalyst concentration from 100 to 3000 wppm in the reaction medium; or a combination thereof.

16. The process of claim 1, further comprising controlling an ethyl iodide concentration in the reaction medium at less than or equal to 750 wppm.

17. The process of claim 16, wherein the propionic acid concentration in the product acetic acid is less than 250 wppm, without directly removing propionic acid from the product acetic acid;
wherein ethyl iodide in the reaction medium and propionic acid in the acetic acid product are present in a weight ratio from 3:1 to 1:2;
wherein acetaldehyde and ethyl iodide are present in the reaction medium in a weight ratio from 2:1 to 20:1;
wherein an ethanol concentration in the methanol feed into the reactor is less than 150 wppm; or a combination thereof.

18. The process of claim 17, wherein the ethyl iodide concentration in the reaction medium is controlled by adjusting at least one of a hydrogen partial pressure in the carbonylation reactor, a methyl acetate concentration in the reaction medium, and a methyl iodide concentration in the reaction medium.

19. The process of claim 1, wherein the first treatment device, the second treatment device, or both individually comprise a plurality of the sampling ports arranged longitudinally at essentially equal intervals along at least a portion of the side of the corresponding treatment device.

* * * * *